(12) United States Patent
Zhang

(10) Patent No.: US 11,564,563 B2
(45) Date of Patent: Jan. 31, 2023

(54) APPARATUS AND METHOD OF A MULTIFUNCTIONAL OPHTHALMIC INSTRUMENT

(71) Applicant: Aizhong Zhang, Rochester, NY (US)

(72) Inventor: Aizhong Zhang, Rochester, NY (US)

( * ) Notice: Subject to any disclaimer, the term of this patent is extended or adjusted under 35 U.S.C. 154(b) by 208 days.

(21) Appl. No.: 16/278,087

(22) Filed: Feb. 16, 2019

(65) Prior Publication Data
US 2019/0254515 A1 Aug. 22, 2019

Related U.S. Application Data

(60) Provisional application No. 62/631,772, filed on Feb. 17, 2018.

(51) Int. Cl.
*A61B 3/10* (2006.01)
*A61B 3/00* (2006.01)
*A61B 3/14* (2006.01)

(52) U.S. Cl.
CPC ............ *A61B 3/101* (2013.01); *A61B 3/0008* (2013.01); *A61B 3/0091* (2013.01); *A61B 3/145* (2013.01)

(58) Field of Classification Search
CPC .... A61B 3/10; A61B 3/00; A61B 3/14; A61B 3/101; A61B 3/0008; A61B 3/0091; A61B 3/3145; A61B 3/102; A61B 3/1005; A61B 3/1015; A61B 3/0025; A61B 3/112; A61B 3/145; G02B 9/34; G02B 9/36; G02B 15/144; G02B 156/144105
USPC ....... 351/221, 200, 206, 208, 210, 211, 212, 351/214, 239; 359/686, 688, 773
See application file for complete search history.

(56) References Cited

U.S. PATENT DOCUMENTS

| 3,248,162 A | 4/1966 | Knoll |
| 4,591,244 A * | 5/1986 | Aono ............ G02B 15/144109 359/688 |
| 5,110,200 A | 5/1992 | Snook |

(Continued)

OTHER PUBLICATIONS

Schulze, Mark E., Natalie Hutchings, Trefford Simpson "Grading bulbar redness using cross-calibrated clinical grading scales" Investigative Ophth & Vis Sci 52, No. 8 (2011).

(Continued)

*Primary Examiner* — Jie Lei
(74) *Attorney, Agent, or Firm* — Lynne M. Blank, Esq.

(57) ABSTRACT

A multifunctional ophthalmic instrument and method for assessing ocular surface health is disclosed. The instrument includes an illumination projector, which contains broadband light sources, covering visible and near infrared spectra, a zoom lens system with continuously variable magnification, a detection system to record said images, and a computer to display and analyze said images. Preferably, an eye alignment system with a beamsplitter is used to provide a fixation target for the eye under assessment. An optional thermal camera, operating in the long wave infrared spectrum is aligned paraxially to the zoom lens system. Further, an optional separate video camera is used to monitor the blink rate. Corneal topography and tear break up time could be evaluated with a low magnification, and microscopic features, such as tear meniscus height, meibomian gland orifices, are imaged at a high magnification. Meibomian glands and lipid layer thickness are analyzed with visible and near infrared spectra.

21 Claims, 27 Drawing Sheets

(56) References Cited

U.S. PATENT DOCUMENTS

| | | | |
|---|---|---|---|
| 5,349,398 | A | 9/1994 | Koester |
| 5,500,697 | A | 3/1996 | Fujieda |
| 5,684,562 | A | 11/1997 | Fujieda |
| 5,841,511 | A | 11/1998 | D'Souza et al. |
| 5,864,383 | A | 1/1999 | Turner et al. |
| 6,045,503 | A | 4/2000 | Grabner et al. |
| 6,053,614 | A * | 4/2000 | Kawamura .......... A61B 3/1173 351/205 |
| 6,601,956 | B1 | 8/2003 | Jean et al. |
| 6,692,126 | B1 | 2/2004 | Xie et al. |
| 7,121,666 | B2 | 10/2006 | Tseng et al. |
| 7,611,245 | B2 | 11/2009 | Carbonari |
| 7,866,819 | B2 | 1/2011 | Tuan |
| 7,976,163 | B2 * | 7/2011 | Campbell .............. A61B 3/107 351/212 |
| 8,192,026 | B2 * | 6/2012 | Gravely ................ A61B 3/101 351/221 |
| 8,249,695 | B2 | 8/2012 | Grenon et al. |
| 8,591,033 | B2 | 11/2013 | Korb et al. |
| 8,820,935 | B2 | 9/2014 | Steinmueller |
| 8,899,753 | B2 | 12/2014 | Steinmueller |
| 9,019,620 | B2 * | 4/2015 | Masui ............ G02B 15/144515 359/689 |
| 2011/0273550 | A1 | 11/2011 | Amano et al. |
| 2017/0276915 | A1 * | 9/2017 | Tomioka .............. G02B 15/173 |
| 2018/0161579 | A1 * | 6/2018 | Franke ................... A61B 5/389 |

OTHER PUBLICATIONS

J. Mackinven, C.L. McGuinness, E. Pascal, R.L. Woods "Clinical grading of the upper palpebral conjunctiva of noncontact lens wearers" Opt. & Vis. Sci. 78, No. 1 (2001): 13-18.

Pult, Heiko and Jason J. Nichols "A review of meibography" Optometry and Vision Science 89, No. 5 (2012): E760-E769.

E. Arita, K. Itoh, K. Inoue, S Amano "Noncontact infrared meibography to document age-related changes of the meibomian glands in a normal population" Ophth 115, No. 5 (2008).

Ngo, William, Srutho Srinivasan, Lyndon Jones "Historical overview of imaging the meibomian glands" Journal of Optometry 6, No. 1 (2013): 1-8.

Wise, Ryan J., Rachel K. Sobel, Richard C. Allen "Meibography: a review of techniques and technologies" Saudi Journal of Ophthalmology 26, No. 4 (2012): 349-356.

Bron, A.J., L. Benjamin, G.R. Snibson "Meibomian gland disease: classification and grading of lid changes" Eye 5, No. 4 (1991): 395.

Zhang, Salahura, Kottaiyan, Yoon, Aquavella, Zavislan "Multimodal imaging of ocular surface of dry eye subjects" In Multimodal Biomed Imag XI, vol. 9701, p. 97010H, ISOP, 2016.

Goto, Dogru, Kojima, Tsubota "Computer-synthesis of an interference color chart of human tear lipid layer by a colorimetric approach" Inv Ophth & Vis Sci 44, No. 11 (2003) 4693.

A. Bron, J. Tiffany, S. Gouveia, N. Yokoi, L. Voon "Functional aspects of the tear film lipid layer" Experimental Eye Research 78, No. 3 (2004): 347-360.

King-Smith, Ewen, Fink, Fogt, Nichols, Hill, Wilson "The thickness of the human pre-corneal tear film: evidence from reflection spectra" Inv Ophth & Vis Sci 41, No. 11 (2000).

Zhang, Maki, Salahura, Kottaiyan, Yoon, Hindman, Aquavella, Zavislan "Thermal analysis of dry eye subjects and the thermal impulse perterbation model of ocular surface".

Abreu, Callan, Kottaiyan, Zhang, Yoon, Aquavella, Zavislan, Hindman "Temperatures of the Ocular Surface, Lid, and Periorbital Regions of Sjorgens, Evaporative and aqueous . . . ".

Tsubota, Kazuo and Katsu Nakamori "Effects of ocular surface area and blink rate on tear dynamics" Archives of Ophthalmology 113, No. 2 (1995): 155-158.

Nakamori, Odawara, Nakajima, Mizutani, Tsubota "Blinking is controlled primarily by ocular surface conditions" American Journal of Ophthalmology 124, No. 1 (1997): 24-30.

Tsubota, Hata, Okusawa, Egami, Ohtsuki, Nakamori "Quantitative videographic analysis of blinking in normal subjects and patients with dry eye" Arch of Ophth 114, No. 6 (1996).

R.J. Braun, T.A. Driscoll, C.G. Begley, P.E. King-Smith, J.I. Siddique "On tear film breakup (TBU): dynamics and imaging" Math Medicine & Biology, JIMA 35, No. 2 (2017): 145-180.

Craig, J.P., K. Blades, S. Patel "Tear lipid layer structure and stability following expression of the meibomian glands" Ophth & Physio Optics 15, No. 6 (1995): 569-574.

LS Mengher, AJ Bron, SR Tonge, DJ Gilbert "A non-invasive instrument for the clinical assessment of the clincal assessment of the pre-corneal tear film stability" Current Eye Res. 4, No. 1 (1985): 1-7.

Cho, Pauline "Reliability of a portable noninvasive tear break-up time test on Hong Kong—Chinese" Optometry & Vision Science 70, No. 12 (1993): 1049-1054.

Mainstone, Julia C., Adrian S. Bruce, and Timothy R. Golding "Tear meniscus measurement in the diagnosis of dry eye" Current Eye Research 15, No. 6 (1996): 653-661.

Kawai, Yamada, Kawashima, Inoue, Goto, Mashima, Tsubota "Quantitative evaluation of tear meniscus height from fluorescein photographs" Cornea 26, No. 4 (2007): 403-406.

N Yokoi, A Bron, J Tiffany, N Brown, J Hsuan and C Fowler "Reflective meniscometry: a noninvasive method to measure tear meniscus curvature" British J of Ophth 83, No. 1 (1999).

Johnson, Michael E., Paul J. Murphy, "The agreement and repeatability of tear meniscus height measurement methods" Optometry & Vision Science 82, No. 12 (2005); 1030-7.

Downie, Laura E., Peter R. Kellar, Algis J. Vingrys "Assessing ocular bulbar redness: a comparison of methods" Ophth. & Physio. Optics 36, No. 2 (2016): 132-9.

Fieguth, Paul and Trefford Simpson "Automated measurement of bulbar redness" Investigative Ophthalmology & Visual Science 43, No. 2 (2002): 340-347.

Mejia-Barbosa, Yobani, and Daniel Malacar-Hernandez, "a review of methods for measuring corneal topography" Optometry and Vision Science 78, No. 4 (2001): 240-253.

Applegate, Raymond A. and Howard C. Howland, "Noninvasive measurement of corneal topography" IEEE Engineering in Medicine and Biology Magazine 14, No. 1, (1995): 30-42.

Levene, John R., "The true inventors of the keratoscope and photo-keratoscope" The British Journal of the History of Science 2, No. 4 (1965): 324-342.

Rand, Howland, and Applegate, "Mathematical model of a placido disk keratometer and its implications for recovery of corneal topography" Optom. & Vision Sci. 74, No. 11 (1997).

Rowsey, James J., A.E. Reynolds, and Randy Brown, "Corneal topography: corneascope" Archives of Opthalmology 99, No. 6 (1981): 1093-1100.

Klein, Stanly A. "Corneal topography reconstruction algorith that avoids the skew ray ambiguity and the skew ray error" Optometry and Vision Sci. 74, No. 11 (1997): 945-962.

Mandell, Robert B. "A guide to videokeratography" International Contact Lens Clinic 23, No. 6 (1996): 205-228.

J.D. Doss, R.L. Hutson, J.J. Rowsey, and D.R. Brown, "Method for calculation of corneal profile and power distribution" Arch Ophth 99, No. 7 (1981): 1261-5.

Halstead, Barsky, Klein, Mandrell "A spline surface algorithm for reconstruction of corneal topography from a videokeratographic reflection patern" Opt & Vis Sci 72, No. 11.

Sweeney, Deborah F., Thomas J. Millar and Shiwani R. Raju "Tear film stability: a review" Experimental Eye Research 117 (2013): 28-38.

* cited by examiner

APPARATUS AND METHOD OF A MULTIFUNCTIONAL OPHTHALMIC INSTRUMENT

CROSS REFERENCE TO RELATED APPLICATIONS

Priority is claimed to Provisional U.S. Patent Application Ser. No. 62/631,772 by A. Zhang filed Feb. 17, 2018 and entitled "Apparatus and method of a multifunctional ophthalmological instrument", the disclosure of which is incorporated herein by reference.

FIELD OF THE INVENTION

This invention relates to the field of ophthalmic instrumentation to assess the health of the eye, in particular, to evaluate the ocular surface health.

BACKGROUND OF THE INVENTION

The ocular surface is the anterior part of an eye and it consists the cornea, limbus, conjunctiva, and tear film. The adjacent structures of the ocular surface, such as the lacrimal gland, the lacrimal drainage apparatus, the eyelids, and the eyelashes, are crucial for the physiological health of the ocular surface.

Tear film is a thin, moist and protective film anterior to the cornea, and it is essential to ocular surface health and visual acuity. Chronic impairment in tear film will lead to dry eye syndrome, which is one of the most common reasons people visit an eye care professional. Patients with dry eye syndrome either cannot secrete enough tears or their tear quality is not good enough. Quantitative measurements of the tear film form the cornerstone for clinical diagnosis and treatment of dry eye subjects.

Tear film is composed of three layers anterior to the corneal epithelial cells, and its thickness is reported to be around 3 μm. The posterior mucous layer contains mucins secreted by the goblets cells in the conjunctiva. The mucous layer forms a viscoelastic matrix to stabilize the tear film on the corneal epithelium. The middle aqueous layer is the major watery part of the tear film, which contains a number of nutrients and proteins related to the immune system, such as globulins, lysozyme, lactoferrin, etc. The aqueous layer is secreted from the lacrimal gland, and it is essential for spreading of the tear film and regulating tear osmolarity. The lipid layer is the most anterior part of the tear film, and its thickness is usually in the order of 1 to 100 nm. It is secreted by the meibomian glands, which are tens of vertical glands lined up inside the tarsal plates of both upper and lower eyelids. The lipid layer serves to prevent and reduce evaporation, and enhance the tear film stability.

Various diagnostic methods have been developed to evaluate the ocular surface. Keratoscope was invented by the Portuguese physician Antonio Placido in 1880, which measures the reflected image off the human cornea of a disk with a central hole, bearing concentric black and white ring patterns. The disk has been referred to as Placido's disk. A large number of variations and improvements of the keratoscope and the corresponding topography reconstruction algorithms have been developed ever since, mainly due to the increasing significance and demand of precise corneal topography measurements for contact lens fitting and keratorefractive surgeries. Projectors with various shapes, colors and ring or mire patterns to replace the original Placido's disk have been described in the prior art, and the basic principle of using the reflected images off the cornea to retrieve the corneal topography remains the same.

Every time after a blink, the tear film is replenished and redistributed, and as the eye remains open for a period of time, the tear film gradually gets thinner, and eventually breaks up at some spots, due to surface tension or evaporation. Clinically, the time interval between the last blink and the first random appearance of a tear break up spot or a dry spot in the tear film is referred to as the tear breakup time (TBUT), and it's indicative of the tear film stability. Conventionally, a TBUT measurement requires the staining of the ocular surface with fluorescein, since the dry spot will be clearly visible under a slit-lamp after the staining. However, it has been reported that the instillation of fluorescein affects the tear stability. Several non-invasive measurement methods of TBUT without staining have been developed to obtain TBUT more objectively, which measure the change in the reflected images off the cornea of a grid or ring pattern, such as the methods taught in "A non-invasive instrument for clinical assessment of the pre-corneal tear film stability." Current eye research 4, no. 1 (1985): 1-7, by Mengher, Lakhbir S., Anthony J. Bron, Stephen R. Tonge, and David J. Gilbert, and "Reliability of a portable noninvasive tear break-up time test on Hong Kong-Chinese." Optometry & Vision Science 70, no. 12 (1993): 1049-1054, by Cho, Pauline.

Tear meniscus height (TMH) measurement is an indirect method to evaluate the tear volume widely used in clinics. A tear meniscus is formed between the eyelid inner surface and the globe of the eye, and along the superior and inferior eye lid margins. It is estimated that the tear menisci holds 75% to 90% of the total tear volume. The larger the tear meniscus height is, the larger the tear volume is. Because of the frequent movement of the upper eyelid, and the obscuration by the eyelashes, usually only the lower tear meniscus is measured clinically. A tear meniscus height of ≤0.2 mm is sometimes chosen to be indicative of dry eye. A number of techniques have been developed to measure TMH. TMH can be measured with or without fluorescein to enhance the contrast, in frontal view or in a cross-sectional view, depending on the technique employed. The simplest TMH measurement is done with a slit lamp, where a reticule is included as part of the eyepiece system. If fluorescein is used, a color filter is usually employed to enhance the contrast. Other than slit lamps, several other instruments such as optical coherence tomography (OCT) systems or optical pachymeters can also be used for TMH evaluation. In an OCT system, TMH is obtained in a cross-sectional image of the anterior part of the eye.

Bulbar hyperemia is often referred to as bulbar redness due to the redness appearance of the eye caused by the vasodilation of the conjunctival blood vessels. Bulbar redness is a common symptom of a number of ophthalmic diseases such as dry eye syndrome, glaucoma, scleritis, keratitis, xerophthalmia and so on. Clinically, bulbar redness is either graded by comparing with reference to standardized descriptions or illustrations by clinicians subjectively, or the images of the eye is analyzed digitally and objectively along an arc, a line or within a selected region of interest (ROI) of the conjunctival image. Similarly, hyperemia of palpebral conjunctiva can also be quantitatively evaluated by imaging everted eyelids and analyzing the palpebral redness.

Meibography uses the different absorption, translucency, and scattering of light by the meibomian glands, compared to adjacent skin tissues, to form an image with high enough contrast to distinguish the meibomian glands distribution within the upper and lower eyelids. Traditionally, there are two types of meibography, one with transillumination, and the other with direct illumination. Meibography was invented by Tapie in 1977 based on clinical tests. Later, infrared light was used to enhance the contrast. The early meibographers usually employed transillumination. In 2008, Arita et al reported a non-contact meibography system that uses direct illumination to collect reflective images. Later, more direct-illumination, non-contact meibographers have been developed, partly because the direct-illumination type is more comfortable for the patients during measurements, compared with the earlier transillumination type.

Biomicroscopy of the inner lid margin has been used to directly inspect individual meibomian gland orifices at the inner side of the eyelids close to the base of eyelashes. With this method, potential obstruction of the meibomian gland orifices by solidified lipids, a condition that might lead to meibomian gland dysfunction, is directly visible to the inspector.

The lipid layer thickness of the tear film can be evaluated based on the reflected pattern of color due to the interference of multiple-reflection at the thin lipid layer. Similar phenomena in daily life include the iridescent colors of a soap bubble, and the colors of a thin oil film on wet ground. The analysis of the reflected color in the red, green and blue color channels in the visible spectrum could quantitatively determine the thickness of the lipid layer. In the prior art, the illumination for lipid layer thickness is limited to visible light, and the reflected color at each pixel is evaluated by comparing the red, green and blue three color channels with theoretical models, such as the apparatus described in U.S. Pat. No. 8,591,033. However, the restriction of the illumination and detection in the visible spectrum for lipid layer thickness measurement limits the accuracy for lipid layer thickness determination in the prior art.

Thermal imaging has been reported to be used to distinguish different types of dry eye syndrome. With the calibration of the thermal emissivity of the eye and the analysis of the temperature cooling pattern after a blink, the thermal dynamical features, including the initial temperature, the steady state temperature and the thermal decay rate could be helpful in dry eye diagnosis.

Blink rate is reported to be indicative for dry eye patients, who tend to have higher blink rate to compensate for the decreased tear supply. Blink rate can be measured by a video camera with large enough field of view and frame rate to detect the downstroke and upstroke of the eyelids movements during a blink.

Even though the aforementioned techniques have been developed independently, there is a need for a novel instrument to integrate these key tear film measurements into one compact device with different system magnifications for different functionalities.

U.S. Pat. Nos. 8,899,753 and 8,820,935 describe a device that integrates some of these aforementioned parameters. However, in the device described in these patents, there are only three possible magnifications achievable. The clinical diagnosis demands a device with a larger magnification range, and with continuously varying magnifications for different ocular surface parameter measurements in order to facilitate clear observation of various regions of interest, and smoothly transit from one target parameter to another.

SUMMARY OF THE INVENTION

It is an object of this invention to integrate multiple key ocular surface measurements into one compact and easy-to-use device.

It is another object of this invention to use a zoom lens system to provide continuous change of magnification in a broad range, so that an operator of the device can adjust the magnification continuously without any gap in magnification changes.

It is another object of this invention to provide a system which can be zoomed in so that fine features in specific areas of clinical interest, such as tear meniscus or individual meibomian gland orifices, can be examined with object resolution of about 0.02 mm or even smaller.

It is another object of this invention to provide a system which can be zoomed out so that the entire eye or at least the majority of the eye under investigation is within a relatively wide field of view, hence features such as corneal topography or bulbar redness can be examined.

It is yet another object of this invention to provide an ocular surface evaluation instrument that can measure the ocular surface thermal evolution simultaneously with the tear break up time measurement.

It is still another object of this invention to use not only infrared light for meibography, but the visible spectrum as well, particularly the red light, to digitally process the image to increase contrast.

It is still another object of this invention to use not only the visible spectrum for lipid layer thickness determination, but the infrared spectrum as well. The lipid layer thickness determination is not based on color match but based on multispectral reflectance match, which will increase the accuracy of the lipid layer thickness measurement.

It is still another object of this invention to include an optional video camera to be placed at the operator's convenience, facing toward the subject, to measure the blink rate.

The present invention relates to a multifunctional ophthalmic instrument for assessing ocular surface health, comprising an illumination projector with an aperture in the posterior end, and the illumination projector contains broadband light sources, covering visible and near infrared spectra, to illuminate an ocular surface and adjacent structures of an eye and project a pattern on the ocular surface; a zoom lens system with continuously variable magnification to form images of the ocular surface and adjacent structures, located posterior to the aperture of the illumination projector; a detection system to record the images, and a computer to display and analyze the images. Preferably, an eye alignment system is used to provide a fixation target for the eye under assessment, which comprises a light source and a beamsplitter, and the beamsplitter is placed between the aperture of the illumination projector and the zoom lens system, and the eye alignment system and the zoom lens system are aligned coaxially. Also preferably, an optional thermal camera, operating in the long wave infrared spectrum is aligned paraxially to the visible and near infrared zoom lens system. An optional separate video camera to monitor the blink rate is connected to the rest of the multifunctional ophthalmic instrument with a wire or wireless connection means.

The invention also includes a method of assessing the ocular surface health using the multifunctional ophthalmic instrument. This method comprising the steps of illuminating an ocular surface and adjacent structures of an eye with an illumination projector, covering visible and near infrared spectra; forming images of the ocular surface and adjacent structures of the eye with the zoom lens system; choosing a magnification by using the zoom lens system; recording images formed on the detector system; displaying and analyzing the images to determine ocular surface health with the computer. Preferably, a subject is requested to fixate on a light source of an eye alignment system, which comprises a light source and a beamsplitter, and the eye alignment system and the zoom lens system are aligned coaxially. Reflected images of the illumination projector off the ocular surface are used to determine the topography of the ocular surface. The time interval between a last blink and an occurrence of a disrupted area of a pattern of reflected images of the illumination projector off the ocular surface is used to determine a tear breakup time. A high magnification is used to inspect microscopic features, such as tear meniscus height, meibomian gland orifices, and bases of eyelashes. The bulbar redness and the palpebral redness of the eye are evaluated based on the conjunctival vascular distribution of recorded images. Meibomian glands imaging is done in the visible and near infrared spectra, and appropriate mathematical index are calculated at each pixel to combine multispectral information to enhance contrast. Lipid layer thickness is evaluated based on multispectral reflectance values of visible and near infrared channels of the detection system. Also preferably, a thermal camera is located paraxially to the zoom lens system and a dynamic thermal change of the ocular surface is analyzed. An optional separate video camera is used to monitor a blink rate of an eye based on a video of movements of the eyelids.

BRIEF DESCRIPTION OF THE DRAWINGS

FIG. 6 also presents three panels of one preferred embodiment of the illumination projector.

DETAILED DESCRIPTION OF THE INVENTION

Figure 1:
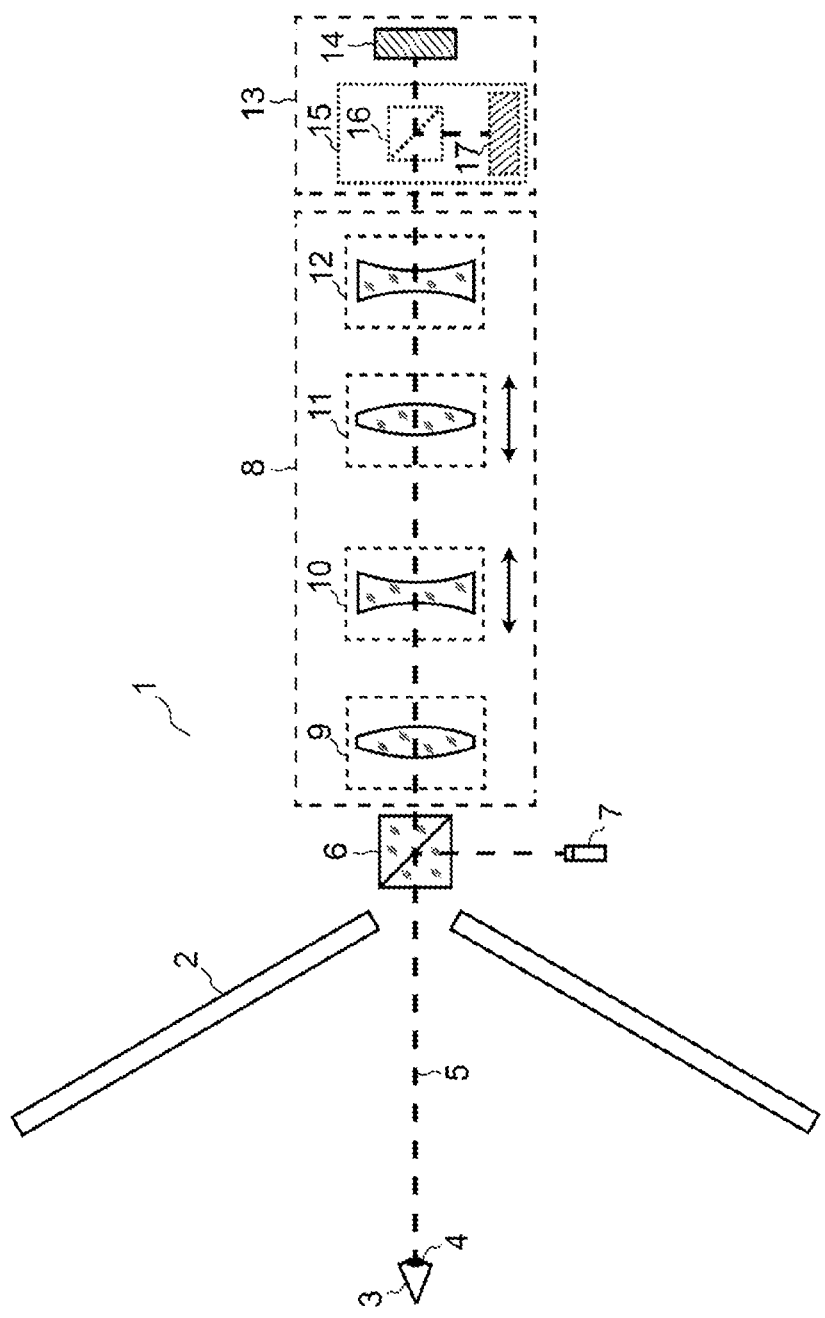
FIG. 1 illustrates the schematic layout of core components of the apparatus for ocular surface assessment.

FIG. 1 illustrates the schematic layout of core components of the multifunctional ophthalmic instrument 1 in this invention. An illumination projector 2 directs light toward an eye 3 and the adjacent structures of the eye of a subject under measurement, and light will get reflected off the ocular surface 4 of the eye. FIG. 1 also indicates an optical axis 5 of the system. An adjustable chin rest and support (not shown in FIG. 1) is preferably used to hold the subject at a comfortable position and maintain stability. Also preferably, an eye alignment system includes a beamsplitter 6 and an alignment light source 7 is aligned coaxially with the optical axis 5, which serves as a fixation target for the subject to focus at, which further improves stability. A zoom lens system 8 with continuous magnification variation is employed to form images of the ocular surface 4 and adjacent tissue structures, which operates in visible and near infrared (NIR) spectra. Even though in the preferred embodiments, the illumination projector and the zoom lens system operate in visible and near infrared spectra, they could also operate in visible to mid-wave infrared wavelength range, or visible to long-wave infrared wavelength range. One embodiment of the zoom lens system is shown in FIG. 1, comprising a positive lens group 9, a negative lens group 10, a positive lens group 11, and a negative lens group 12. Group 9 and 12 are fixed during zoom, while group 10 and 11 are moving during zoom. A detection system 13 is used to record the images formed by the zoom lens system.

Figure 2:
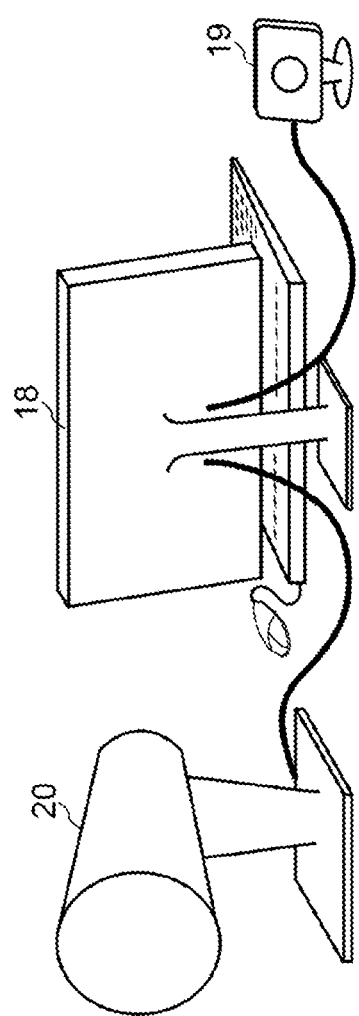
FIG. 2 presents one possible setup of the apparatus in this invention for clinical use.

FIG. 2 presents one embodiment of the setup of the apparatus in this invention for clinical use. A computer 18 with a display is used to monitor the dynamic change of the recorded images in real time, and the computer is used to further analyze the recorded images. The mechanical exterior packaging 20 of the instrument 1 is connected to the computer. An optional separate video camera 19 is used to monitor the blink rate of the subject.

Figure 3:
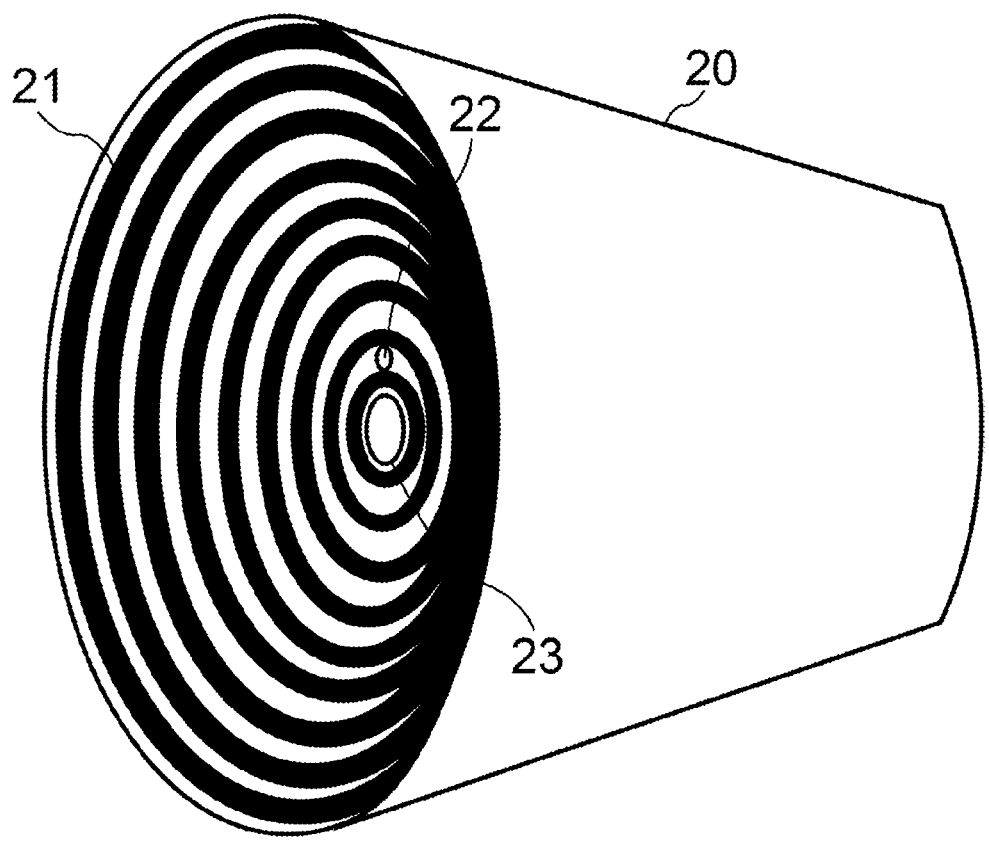
FIG. 3 presents the side view of one embodiment the instrument for ocular surface assessment.

FIG. 3 presents one embodiment of the exterior side view of the instrument 1. In one embodiment of the illumination projector 2, a panel 21 bears black and white concentric ring pattern. A central opening aperture 23 is used for the zoom lens system of visible and near infrared imaging. An opening aperture 22 is used for long wavelength infrared (LWIR) imaging with a micro thermal camera, and one embodiment of the micro thermal camera is the FLIR Lepton micro thermal camera (FLIR Systems, Wilsonville, Oreg.). The micro thermal imaging camera is embedded in the panel 21. The LWIR and the visible/NIR imaging systems are paraxial.

Figure 4:
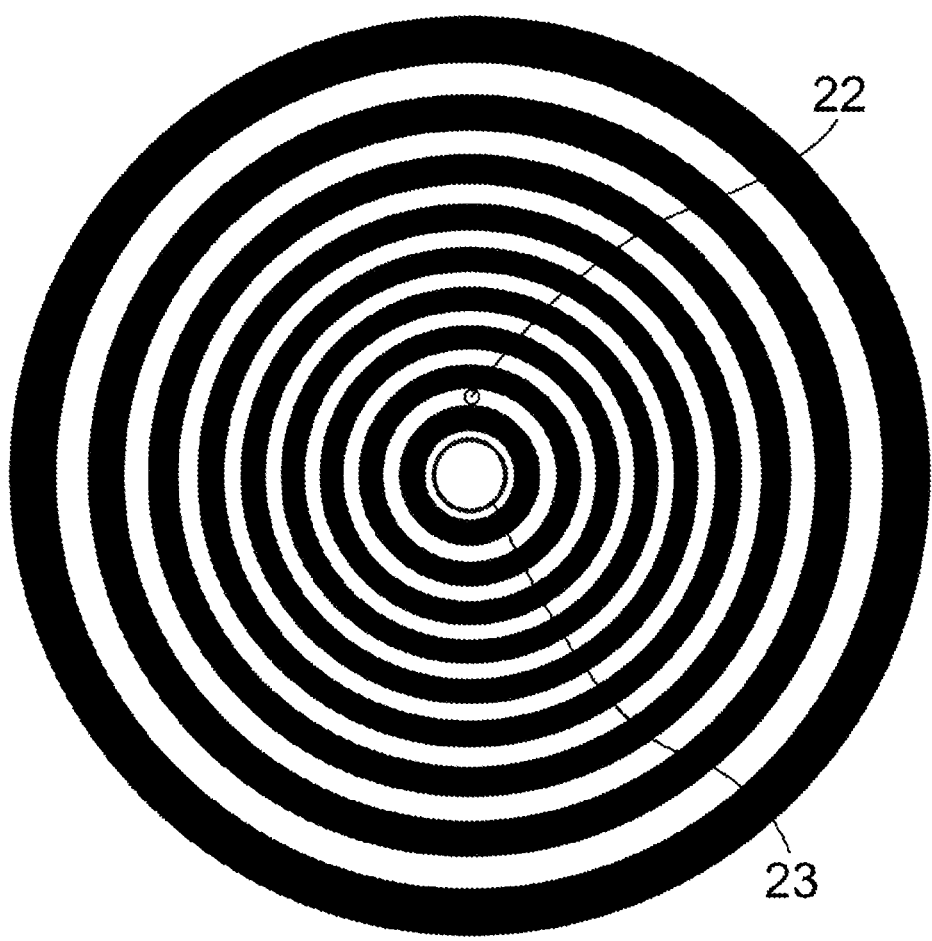
FIG. 4 presents the front view of one embodiment of the illumination projector.

FIG. 4 presents the front view of one embodiment of the illumination projector. The aperture 22 for LWIR imaging with a micro thermal camera is also included.

Figure 5:
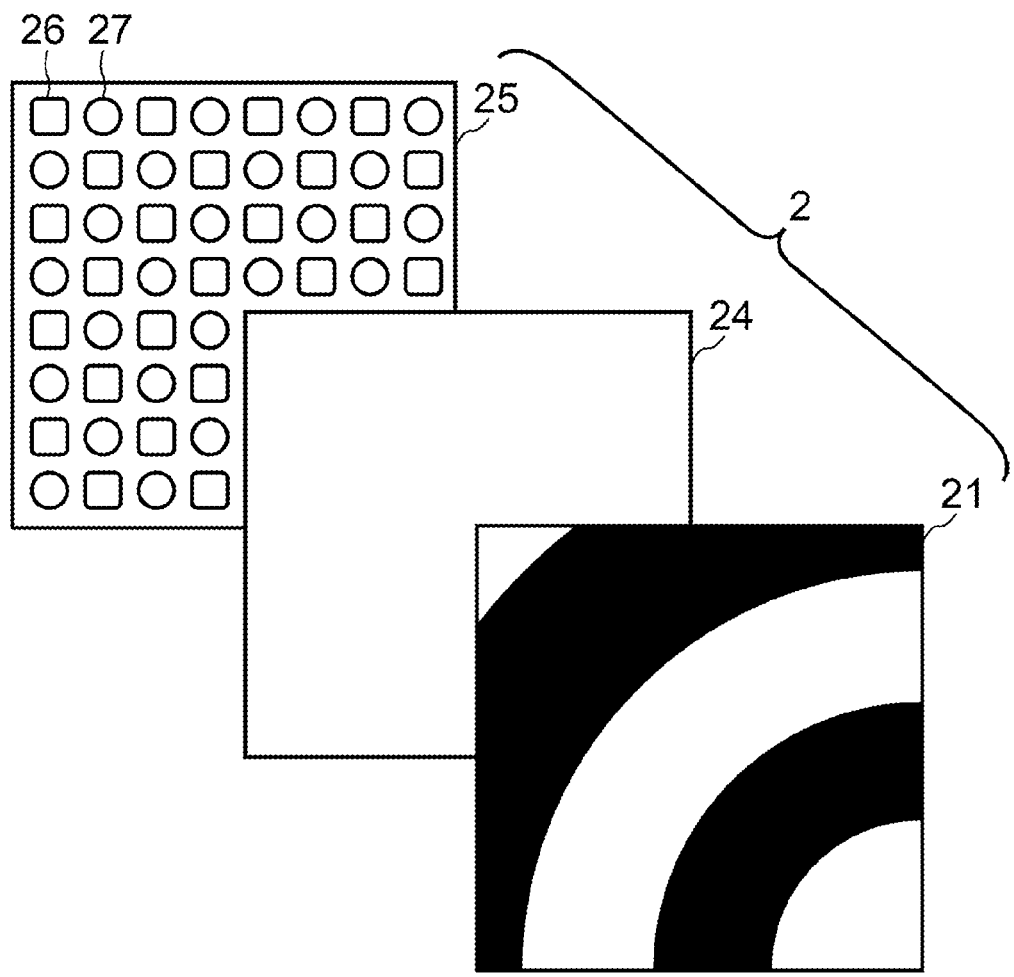
FIG. 5 illustrates the decomposition of the layered structure of three panels of one preferred embodiment of the illumination projector.

The illumination projector 2 has broadband illumination light sources covering the visible and NIR spectra. FIG. 5 illustrates the decomposition of one preferred embodiment of the illumination projector 2. In this embodiment, the illumination projector 2 has a three-layer structure. In the back is an illumination source panel 25 with individual light sources, and one embodiment of these light sources are light-emitting diodes (LEDs), such as the visible white LED array 26 and the NIR LED array 27. Preferably, two sets of broadband light sources are separately controlled, one covering the visible spectrum only, and the other covering the NIR spectrum only. Also preferably, the broadband light sources are arranged in a manner that optimally generates relatively uniform illumination across the illumination panel. In the middle, an optical diffusing panel 24 represents one or multiple layers of translucent materials to generate relatively uniform light output. In the front, structured patterns of the panel 21 are printed or embedded or generated by other similar means, which enables the measurement of corneal topography. There are many possible embodiments of the pattern on the illumination panel, including but not limited to black and white concentric rings with appropriately chosen width of each ring, colorful concentric rings, concentric rings and orthogonal radial lines, etc. In the embodiment of FIG. 5, the panel 21 of the illumination projector 2 bears black and white concentric rings. Further, there are many possible geometric shapes of the illumination projector, including but not limited to a conical frustum, a spherical bowl, or an ellipsoidal bowl.

In another embodiment of the illumination projector 2, a curved OLED display made of organic light-emitting diodes (OLEDs) is used to generate dynamically changing projection patterns. The OLED display operates in both visible and NIR spectra. The dynamically changing projection patterns could improve corneal topography measurement accuracy by moving the edges of the ring or grid patterns to minimize data interpolation during analysis.

Preferably, there is an eye alignment system including a beamsplitter 6 to enable easy alignment of an eye with the instrument, as shown in FIG. 1. The embodiments of the beamsplitter 6 include but are not limited to a cube beamsplitter, a plate beamsplitter, a pellicle beamsplitter, etc. The subject is requested to fixate upon a light source 7 for alignment. The embodiments of the alignment light source 7 include but are not limited to a single LED, an LED with a collimating lens group, a properly positioned optical fiber with a collimating lens group, a low-power or attenuated laser source with the output power density much below maximum permissible exposure (MPE) based on ANSI Z136, etc. The preferred location of the beamsplitter 6 is in front of the zoom lens system 8, or in between the elements of the first zoom lens group 9, if the first zoom lens group is not moving during zoom. In this way, from the perspective of the subject under test, the fixation target size won't be affected by the zoom motion of the following optics, even though the magnification and field of view on the detection system could be continuously changing. On the other hand, placing the beamsplitter 6 in between or behind the zoom lens system 8 but before the detection system 13 is acceptable, but not preferred, due to the variation of the fixation target size during zoom, which will adversely affect the eye alignment. The preferred splitting ratio of the beamsplitter is such that the majority of the light, ~95% for example, enters into the zoom lens system for imaging, and only a small amount of the light, ~5% for example, is used for eye fixation and alignment.

Figure 6:
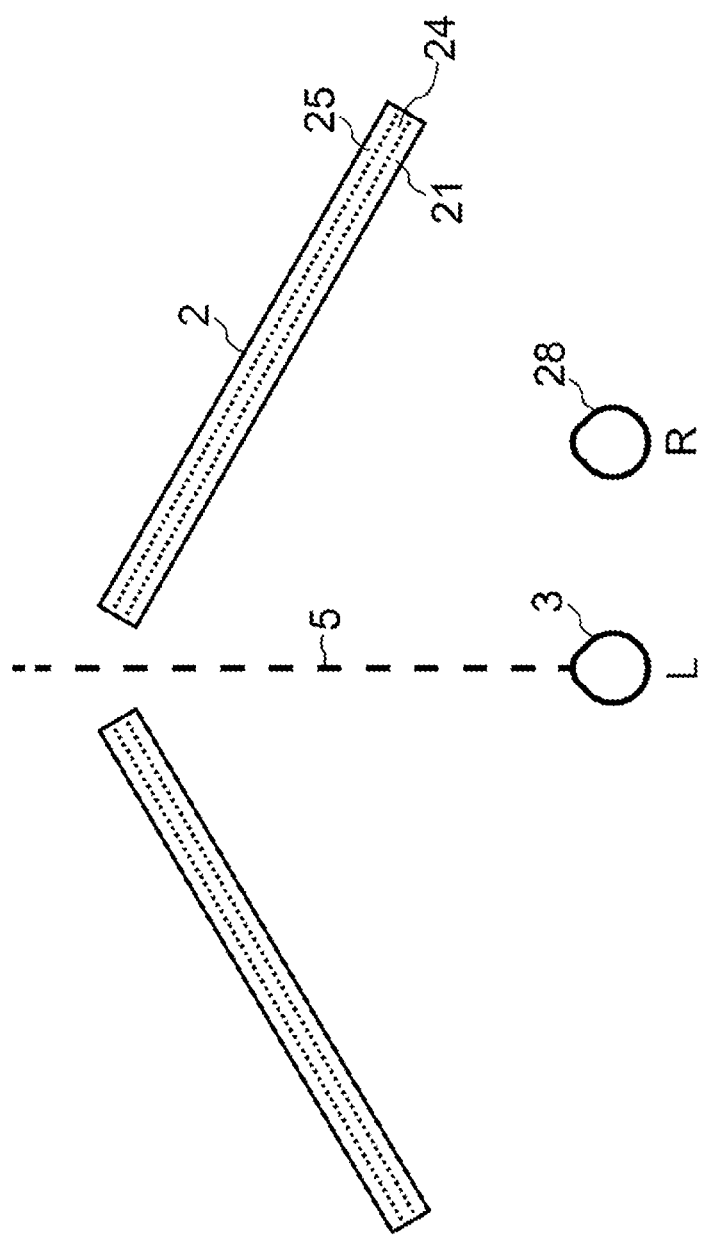
FIG. 6 presents the relative positions of the two eyes of the subject under test to one preferred embodiment of the illumination projector.

FIG. 6 presents the relative positions of the two eyes of the subject under test to one preferred embodiment of the illumination projector, with a horizontal slice view of the illumination projector 2, and this horizontal plane contains the optical axis 5 of the visible and NIR system. The left eye 3 is under test, and 28 is the right eye. If the right eye 28 is under test, the subject's head will be positioned so that the right eye lies on the optical axis 5. FIG. 6 also presents the three-layer structure of one embodiment of the illumination projector 2, of which the detailed structures is shown in FIG. 5. FIG. 6 further presents the relative position of the three panels with the illumination source panel 25 in the back, the optical diffusing panel 24 in the middle, and the panel 21 with a projection pattern in the front.

There are many possible embodiments of the zoom lens system 8. The zoom lens system has at least two moving groups, one is the variator, which changes the magnification or focal length, and the other is the compensator, which keeps the image in focus. One or more fixed groups may be employed to achieve desired system magnification or focal length while helping balance the optical aberrations through zoom. Each group may be divided into more subgroups and a compound zoom lens system with cascading subsystems could be used. Preferably, all zoom lens surfaces are spherical, so that the manufacturing cost is relatively low, and the entire instrument is suitable for volume production.

A detection system follows the zoom lens system, and the total imaging system have a continuous magnification variation capability. Each detector is charge-coupled device (CCD) or complementary metal-oxide-semiconductor (CMOS), or other functionally similar image recording devices. The specific magnification range is determined by the image sensor size and the field of view requirement. Usually, different sensor sizes demand different lens designs to match. To evaluate ocular surface health comprehensively, for an image sensor with a diagonal length of 21.6 mm, the zoom range, in terms of the absolute values of magnifications, is preferably no less than 0.9× to 4.5×, and more preferably no less than 0.72× to 7.2×; for an image sensor with a diagonal length of 6.0 mm, the zoom range is preferably no less than 0.25× to 1.25×, and more preferably no less than 0.2× to 2.0×. The embodiments of the zoom lens system in this invention are all designed to match an image sensor of diagonal length of 6.0 mm Those skilled in the art can easily adjust or scale designs from the disclosure in this invention to match other image sensor sizes.

The detection system can have multiple embodiments. As shown in FIG. 1, in one embodiment, a single detector 14, which has red, green, blue and near infrared four types of pixels are used simultaneously, and it covers both the visible and near infrared spectra. In another embodiment, a complementary subsystem 15 is also used, which includes a dichroic beamsplitter 16, which splits light into a visible branch and a near infrared branch. The detector 14 in this embodiment is only responsive to the visible spectrum with red, green and blue three color channels, and a detector 17 is responsive to the near infrared spectrum. The recorded images on the detection system are further connected to a computer where the images are further processed. The detector 17 could be a monochromatic detector of near infrared spectrum, or it could be a multi-channel near infrared detector, which has separate spectral channels to further divide the near infrared light. For example, it could have 750 nm to 820 nm, 820 nm to 880 nm, and 880 nm to 960 nm three channels. Even though in the preferred embodiment, the detection system 13 includes one visible branch and one near infrared branch with one beamsplitter, more beamsplitters could be used to split light into more branches, for example, it could have three branches: one visible branch, one near infrared branch, and one mid-wave infrared branch.

Figure 7:
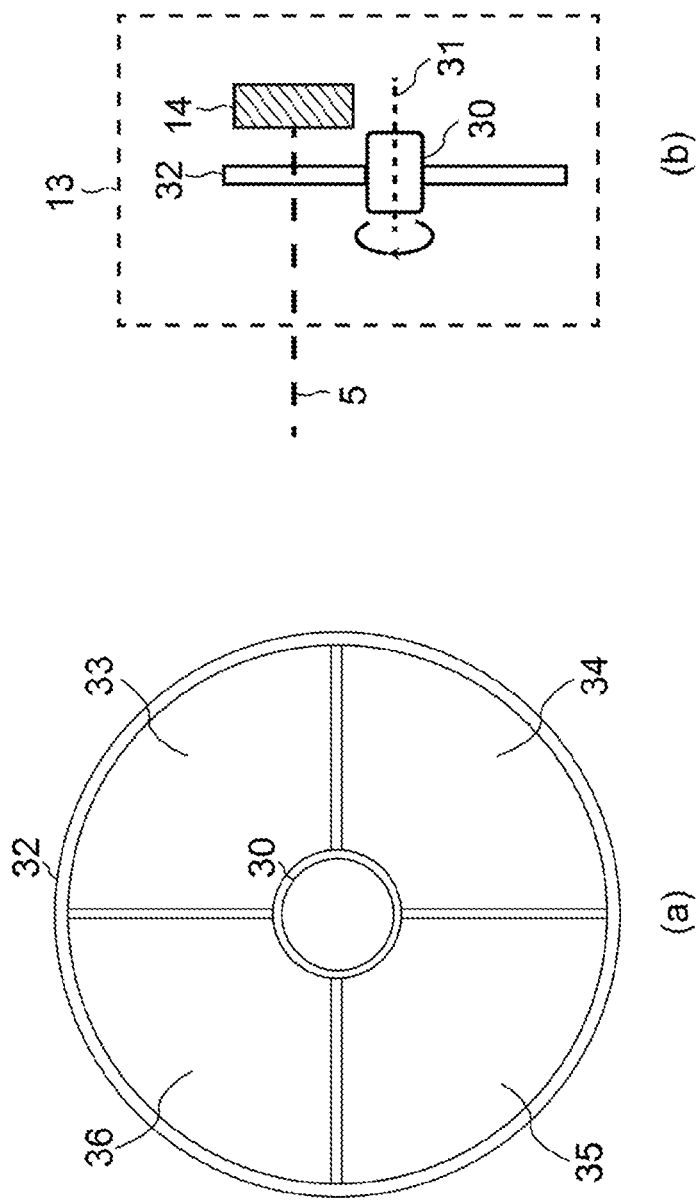
FIG. 7 presents another embodiment of the detector system.

FIG. 7 presents yet another embodiment of the detection system 13, where there is a single detector 14 with red, green and blue three different types of pixels in the visible spectrum, but all or some of the pixels are also responsive to near infrared light as well. FIG. 7(a) is the front view of a rotary wheel 32, with alternating IR-cut filters 33 and 35 and NIR-only filters 34 and 36, and 30 is a rotary motor. FIG. 7(b) is the side view, which shows that the rotary wheel 32 rotates around an axis 31, and an IR-cut filter and an NIR-only filter can be switched alternatively in front of the detector for visible and NIR imaging, such that a sequence of visible-NIR-visible-NIR images series can be taken.

In this invention, four preferred embodiments of the zoom lens system are detailed, although the present invention is not intended to be limited to these embodiments only. All embodiments are designed to match an image sensor with a 6 mm diagonal length. They all have four zoom lens groups with fixed front and back lens groups and two moving groups in the middle. In all four embodiments, the magnification zooms from −2× to −0.2×, hence four 10× zoom lens systems. The zoom motion trajectory is shown for magnifications of −2×, −1.363×, −0.928×, −0.633×, −0.431×, −0.294× and −0.2×, from Zoom 1 to Zoom 7, in a geometrical series for all four embodiments. The stop is set to move along with the third zoom group, and the aperture stop size changes with different zoom positions to maintain a fixed image f/#=15 at all zoom positions. All optical surfaces in all four embodiments are spherical surfaces, including flat surfaces with radius of infinity, in order to control the manufacturing cost for volume production. However, aspherical surface adjustments can be readily added by those skilled in the art. Embodiment 1 and Embodiment 2 are of the PNPN configuration, meaning the effective focal length of the four zoom groups are, in sequence, positive, negative, positive, and negative. Embodiment 3 and Embodiment 4 are of the PNNP configuration, meaning the effective focal length of the four zoom groups are, in sequence, positive, negative, negative, and positive. Embodiment 1 and 3 are optimized with visible and near infrared wavelengths up to 850 nm, while Embodiment 2 and 4 are optimized with visible and near infrared wavelengths up to 940 nm. There is enough spacing, larger than 40 mm, between the last surface of the last zoom lens group and the detector plane in each of the four embodiments for an optional dichroic prism or a rotary color filter wheel. If a dichroic prism is used in the detection system, the embodiments can be readily adjusted by those skilled in the art. These listed embodiments are illustrative, and are by no means the only possible embodiments within the scope of this invention.

Embodiment 1

Figure 8:
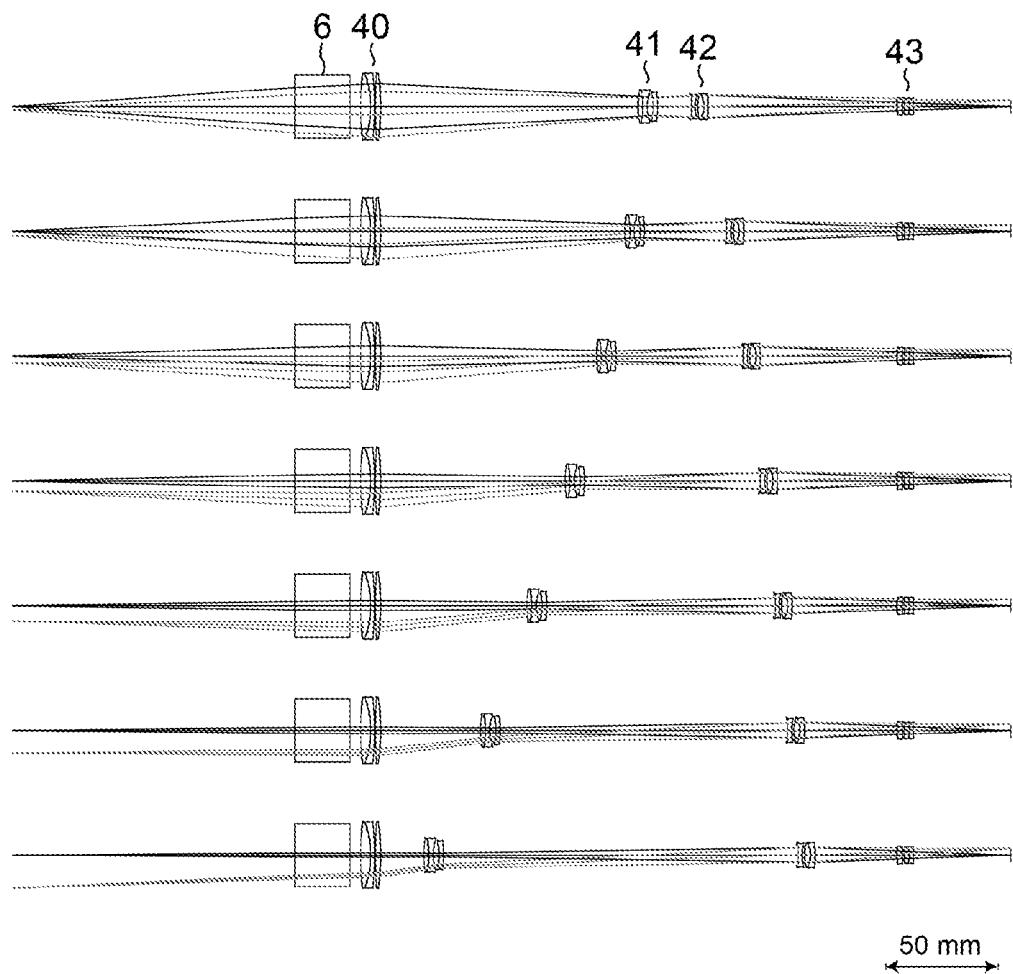
FIG. 8 presents the zoom motion trajectory of Embodiment 1 of a PNPN zoom lens system optimized for visible and near infrared spectra up to 850 nm.
Figure 9:
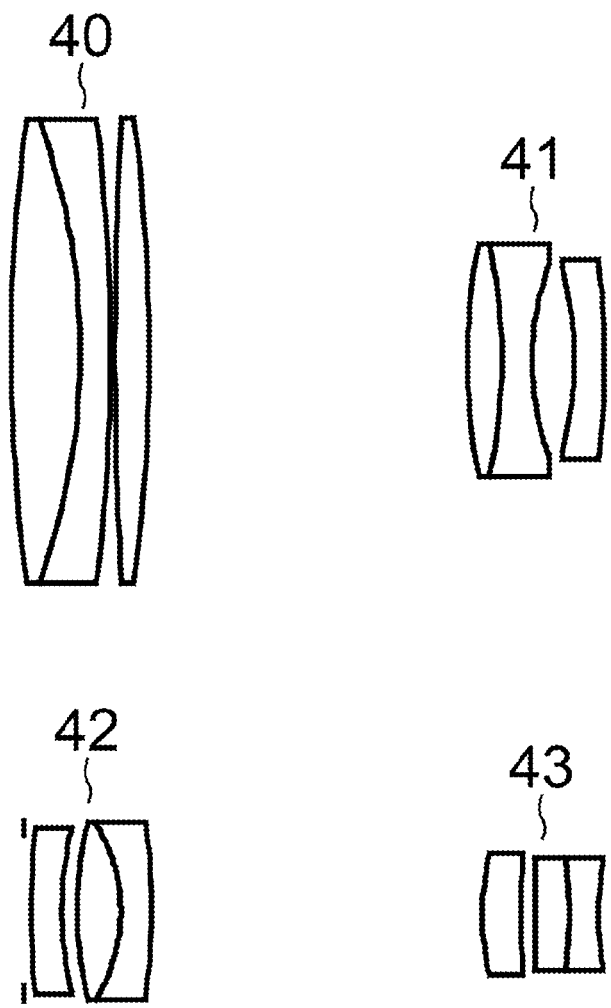
FIG. 9 represents the detailed design forms of each lens group in Embodiment 1.

FIG. 8 presents the zoom motion trajectory of Embodiment 1 of the zoom lens system optimized for visible and near infrared spectra up to 850 nm, for a sensor with the diagonal length of 6 mm. The zoom motion trajectory in FIG. 8 is shown for magnifications of −2×, −1.363×, −0.928×, −0.633×, −0.431×, −0.294× and −0.2×, from Zoom 1 to Zoom 7. This embodiment comprises four zoom groups. 40 is Group 1, and its position is fixed. 41 is Group 2, which is moveable during zoom. 42 is Group 3, which is moveable during zoom. 43 is Group 4 and its position is fixed. This specific embodiment of the four zoom groups has a PNPN configuration. FIG. 9 represents the detailed design forms of each lens group in FIG. 8.

The numerical details of Embodiment 1 are listed in Table 1, and the length values are in units of mm. The variable data during zoom are also listed.

TABLE 1

| Surface Number | Radius of curvature | Thickness | $n_d$ | $V_d$ | Semi-Aperture |
|---|---|---|---|---|---|
| Object | Infinity | 120 | | | |
| 1 | Infinity | 10 | | | 11.30 |
| 2 | Infinity | 25.4 | 1.516800 | 64.1673 | 11.97 |
| 3 | Infinity | 5 | | | 13.32 |
| 4 | 112.1696 | 4.5643 | 1.496999 | 81.5459 | 13.79 |
| 5 | −44.2363 | 2 | 1.834000 | 37.1605 | 13.81 |
| 6 | −126.7120 | 0.3 | | | 14.05 |
| 7 | 254.1522 | 2.2665 | 1.607381 | 56.6501 | 14.10 |
| 8 | −114.1330 | D8 | | | 14.10 |
| 9 | 37.9046 | 2.2819 | 1.834000 | 37.1605 | 6.92 |
| 10 | −35.7130 | 2 | 1.607381 | 56.6501 | 6.76 |
| 11 | 18.0754 | 2.7992 | | | 5.96 |
| 12 | −21.9610 | 2 | 1.810000 | 40.925 | 5.82 |
| 13 | −47.0347 | D13 | | | 5.94 |
| 14-Stop | Infinity | 0.5 | | | SA14 |
| 15 | 71.1545 | 2 | 1.755500 | 45.6608 | 4.95 |
| 16 | 22.8319 | 1 | | | 4.96 |
| 17 | 23.3757 | 2.8762 | 1.607381 | 56.6501 | 5.15 |
| 18 | −10.9471 | 2 | 1.613360 | 44.4937 | 5.18 |
| 19 | −51.0144 | D19 | | | 5.26 |
| 20 | 18.0973 | 2.5 | 1.508469 | 61.1878 | 3.62 |
| 21 | 35.4579 | 1 | | | 3.44 |
| 22 | 567.3298 | 2.2 | 1.581440 | 40.8513 | 3.38 |
| 23 | −27.7453 | 2 | 1.607381 | 56.6501 | 3.28 |
| 24 | 28.1853 | 44.9881 | | | 3.17 |
| 25-Image | Infinity | | | | 3.01 |

| Variable data | | | | | |
|---|---|---|---|---|---|
| Zoom | Magnification | Object full diagonal length | Stop semi-aperture (SA14) | D8 | D13 | D19 |
| Z1 | −2X | 3.00 | 4.90 | 118.7536 | 15 | 86.9583 |
| Z2 | −1.363X | 4.40 | 4.35 | 112.7536 | 37.3408 | 70.6175 |
| Z3 | −0.928X | 6.46 | 4.09 | 99.6119 | 58.1627 | 62.9373 |
| Z4 | −0.633X | 9.49 | 3.82 | 85.1173 | 80.5433 | 55.0513 |
| Z5 | −0.431X | 13.92 | 3.59 | 67.5491 | 104.8821 | 48.2808 |
| Z6 | −0.294X | 20.44 | 3.39 | 46.1360 | 132.0300 | 42.5459 |
| Z7 | −0.2X | 30.00 | 3.23 | 20 | 163.0117 | 37.7002 |

The overall length of Embodiment 1 from the front surface of the beamsplitter (Surface 2) to the image plane is 330.4 mm From the object side to the image side, Surface 1 is a dummy surface, where the edge of the central opening aperture 23 of the illumination projector 2 is located. Surfaces 2 to 3 is the preferred beamsplitter for the eye alignment system. Surfaces 4 to 8 comprise Group 1; Surfaces 9 to 13 comprise Group 2; Surface 14 is the aperture stop; Surfaces 15 to 19 comprise Group 3; Surfaces 20 to 24 comprise Group 4; Surface 25 is the image plane. The spacing between the end of Group 4 (Surface 24) and the image plane is 44.99 mm, large enough to place an optional beamsplitter or rotary wheel of the detection system. The aperture stop diameter changes its size through zoom to maintain a fixed image f/#=15, and it's located at a fixed distance to Group 3, and moves along with Group 3 during the zoom motion.

Figure 10:
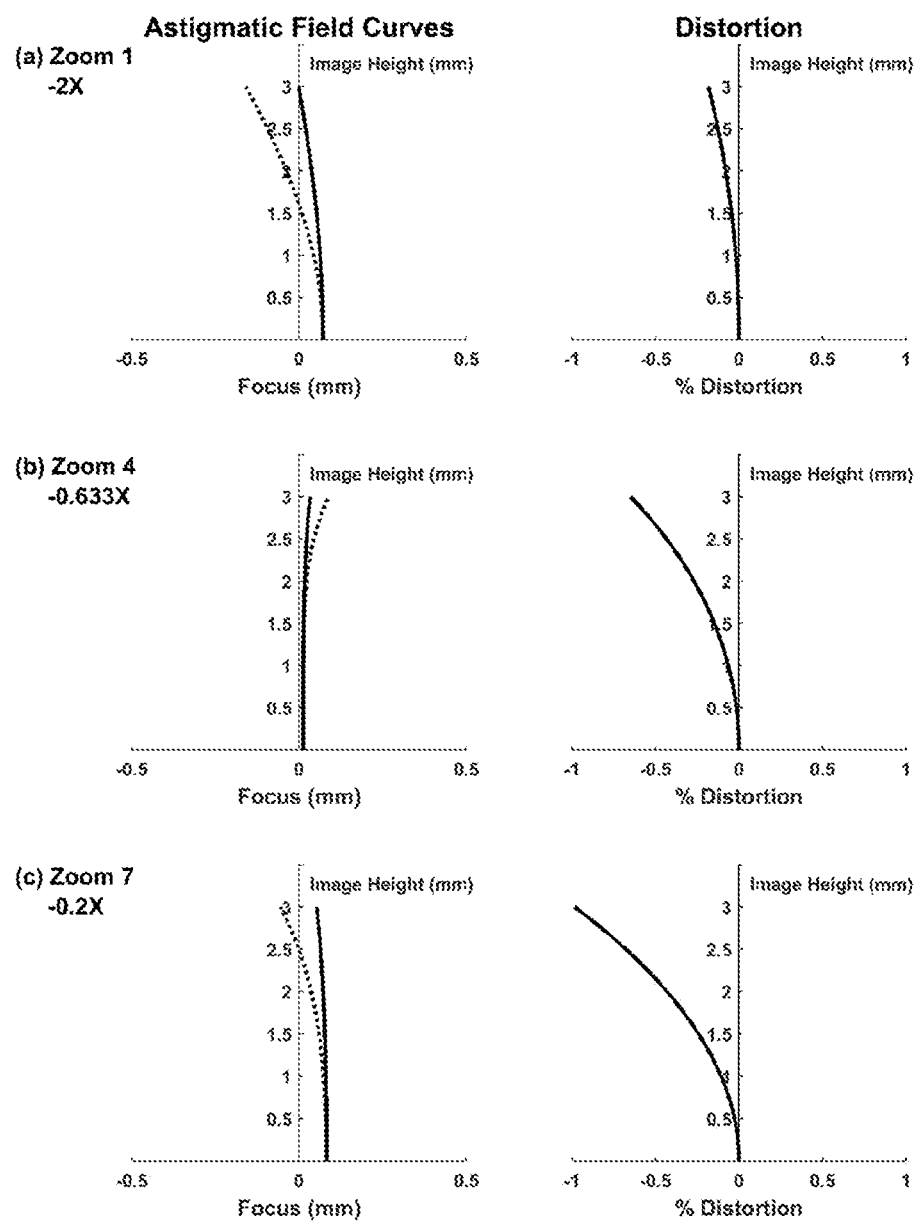
FIG. 10 a-c present astigmatic field curves and distortion of the Embodiment 1 at three representative zoom positions: Zoom 1 (−2×), Zoom 4 (−0.633×) and Zoom 7 (−0.2×).

FIG. 10 a-c present the Embodiment 1 astigmatic field curves on the left and distortion on the right at three representative zoom positions: Zoom 1 (-2×), Zoom 4 (-0.633×) and Zoom 7 (-0.2×). In the field curves, the dashed line is for tangential field points, and the solid line is for sagittal field points.

Figure 11:
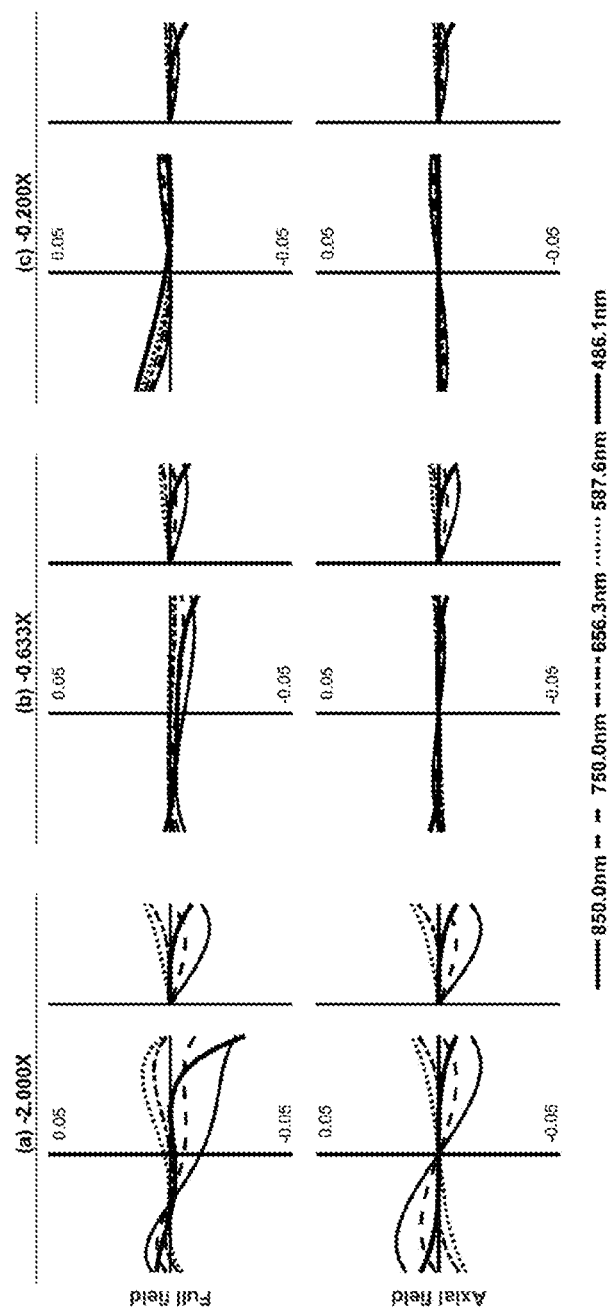
FIG. 11 a-c present the transverse ray plots of Embodiment 1 at three zoom positions. The overlap of some wavelengths with transverse ray errors close to zero at some subplots indicates good color aberration correction.

FIG. 11 a-c present the transverse ray plots of Embodiment 1 at the axial and full field points of three representative zoom positions: Zoom 1 (-2×), Zoom 4 (-0.633×) and Zoom 7 (-0.2×). For each zoom position, the tangential fields are on the left, and the sagittal fields are on the right. The overlap of some wavelengths with transverse ray errors close to zero at some subplots indicates good color aberration correction.

Figure 12:
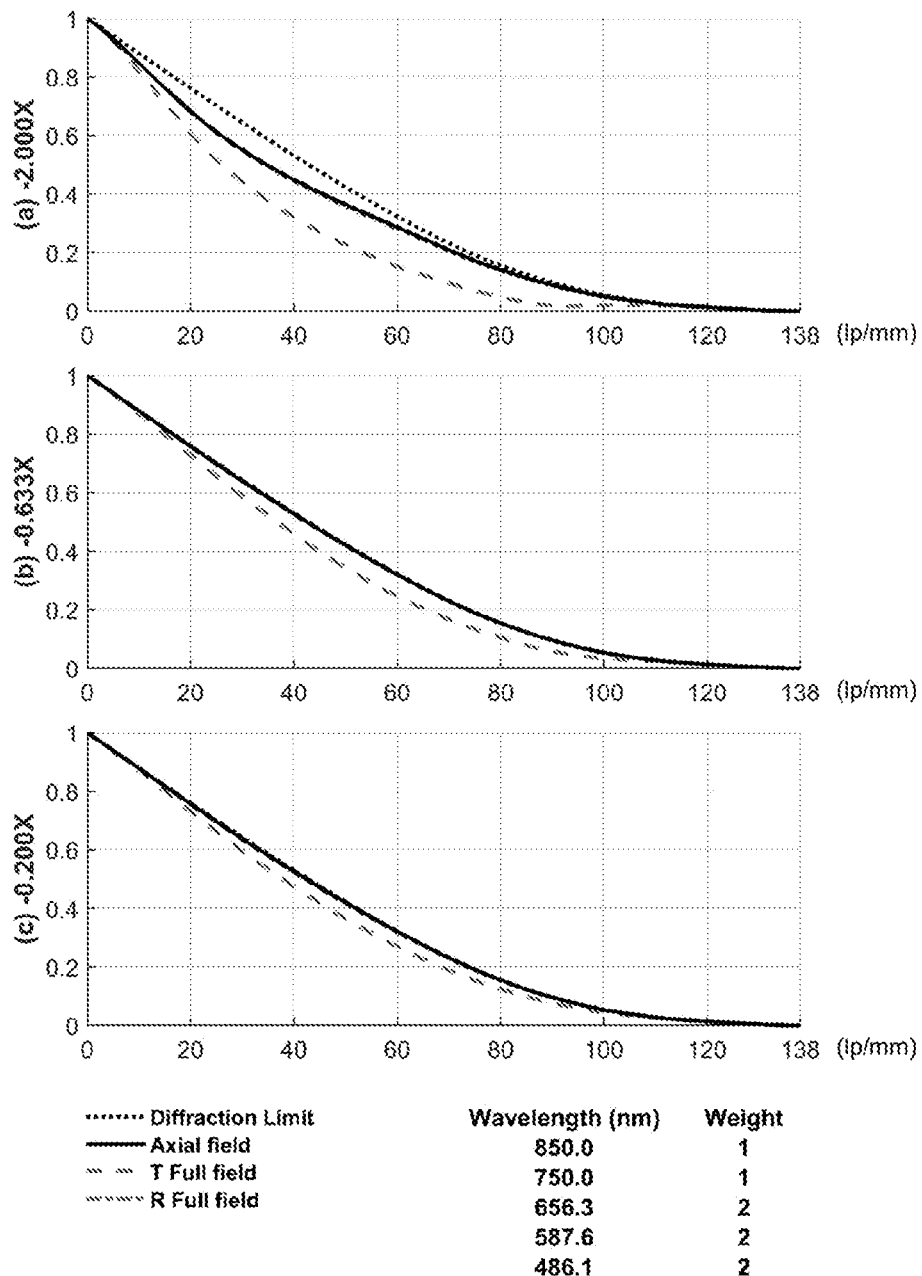
FIG. 12 presents the modulation transfer function (MTF) plots of Embodiment 1 at three zoom positions.

FIG. 12 presents the modulation transfer function (MTF) plots of Embodiment 1 of three representative zoom positions: Zoom 1 (-2×), Zoom 4 (-0.633×) and Zoom 7 (-0.2×).

Embodiment 2

Figure 13:
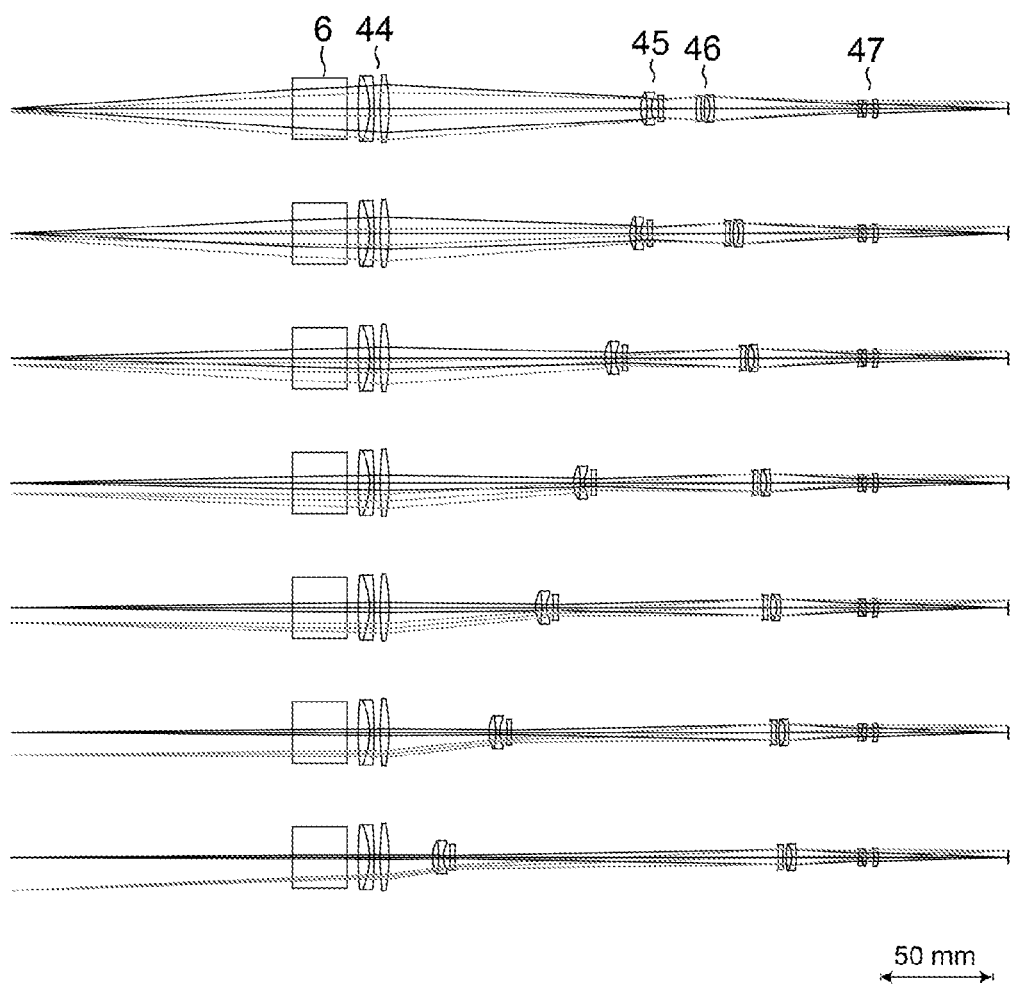
FIG. 13 presents the zoom motion trajectory of Embodiment 2 of a PNPN zoom lens system optimized for visible and near infrared spectra up to 940 nm.
Figure 14:
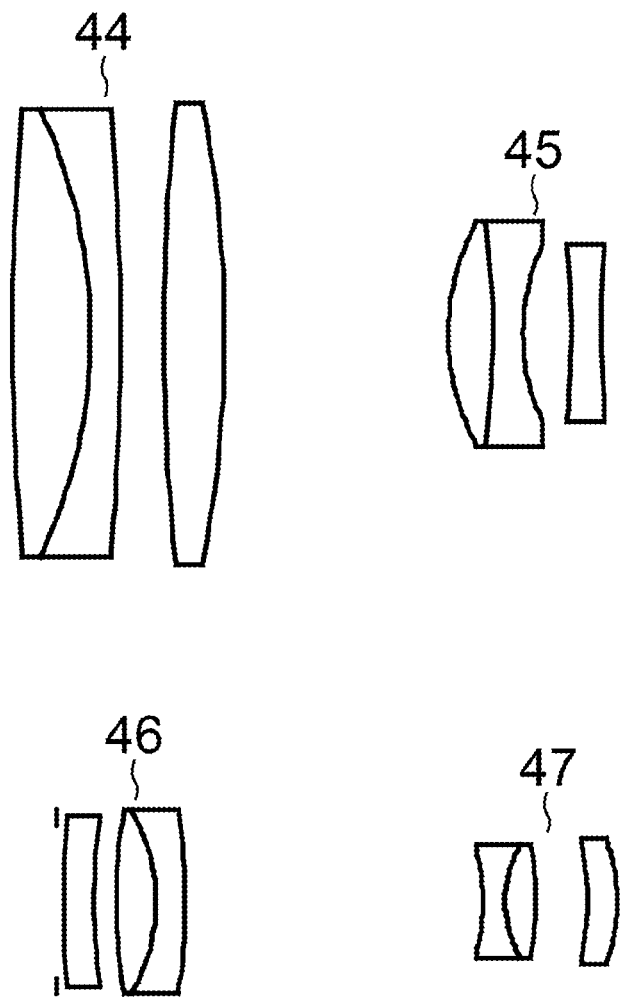
FIG. 14 represents the detailed design forms of each lens group in Embodiment 2.

FIG. 13 presents the zoom motion trajectory of Embodiment 2 of the zoom lens system optimized for visible and near infrared spectra up to 940 nm, for a sensor with the diagonal length of 6 mm. The zoom motion trajectory in FIG. 13 is shown for magnifications of -2×, -1.363×, -0.928×, -0.633×, -0.431×, -0.294× and -0.2×, from Zoom 1 to Zoom 7. This embodiment comprises four zoom groups. 44 is Group 1, and its position is fixed. 45 is Group 2, which is moveable during zoom. 46 is Group 3, which is moveable during zoom. 47 is Group 4 and its position is fixed. This specific embodiment of the four zoom groups has a PNPN configuration. FIG. 14 represents the detailed design forms of each lens group in FIG. 13.

The numerical details of Embodiment 2 are listed in Table 2, and the length values are in units of mm. The variable data during zoom are also listed.

TABLE 2

| Surface Number | Radius of curvature | Thickness | $n_d$ | $V_d$ | Semi-Aperture |
|---|---|---|---|---|---|
| Object | Infinity | 120 | | | |
| 1 | Infinity | 10 | | | 11.29 |
| 2 | Infinity | 25.4 | 1.516800 | 64.1673 | 11.66 |
| 3 | Infinity | 5 | | | 12.97 |
| 4 | 155.4041 | 5.2444 | 1.496999 | 81.5459 | 13.40 |
| 5 | -34.8075 | 2 | 1.806100 | 40.8999 | 13.45 |
| 6 | -173.5470 | 2.9373 | | | 13.82 |
| 7 | 151.6746 | 4.0869 | 1.607381 | 56.6501 | 14.22 |
| 8 | -78.5003 | D8 | | | 14.27 |
| 9 | 15.6229 | 3 | 1.581440 | 40.8513 | 6.81 |
| 10 | -48.6698 | 2 | 1.607381 | 56.6501 | 6.55 |
| 11 | 13.5534 | 3.2872 | | | 5.62 |
| 12 | -53.6109 | 2 | 1.743972 | 44.8504 | 5.37 |
| 13 | 80.7320 | D13 | | | 5.28 |
| 14-Stop | Infinity | 0.5 | | | 5.11 |
| 15 | 67.3038 | 2 | 1.749502 | 34.9506 | 5.17 |
| 16 | 35.3756 | 1.5 | | | 5.19 |
| 17 | 35.5924 | 2.6804 | 1.572500 | 57.5493 | 5.39 |
| 18 | -12.2110 | 2 | 1.613360 | 44.4937 | 5.42 |
| 19 | -34.9167 | D19 | | | 5.53 |
| 20 | -12.5415 | 1.5 | 1.613360 | 44.4937 | 3.16 |
| 21 | 7.4999 | 2 | 1.608631 | 46.5974 | 3.36 |
| 22 | -27.6996 | 3.5 | | | 3.44 |
| 23 | -18.7089 | 2 | 1.548140 | 45.7501 | 3.60 |
| 24 | -12.6960 | 59.9864 | | | 3.78 |
| 25-Image | Infinity | | | | 3.01 |

| | | Variable data | | | |
|---|---|---|---|---|---|
| Zoom | Magnification | Object full diagonal length | Stop semi-aperture (SA14) | D8 | D13 | D19 |
| Z1 | -2X | 3.00 | 5.11 | 116.0665 | 15.0000 | 66.6973 |
| Z2 | -1.363X | 4.40 | 4.48 | 111.0665 | 33.3971 | 53.3002 |
| Z3 | -0.928X | 6.46 | 4.15 | 99.5574 | 51.9813 | 46.2252 |
| Z4 | -0.633X | 9.49 | 3.88 | 85.1812 | 72.0083 | 40.5743 |
| Z5 | -0.431X | 13.92 | 3.66 | 67.5699 | 94.2618 | 35.9321 |
| Z6 | -0.294X | 20.44 | 3.48 | 46.1148 | 119.5602 | 32.0888 |
| Z7 | -0.2X | 30.00 | 3.33 | 20.0000 | 148.8676 | 28.8962 |

The overall length of Embodiment 2 from the front surface of the beamsplitter (Surface 2) to the image plane is 330.4 mm From the object side to the image side, Surface 1 is a dummy surface, where the edge of the central opening aperture 23 of the illumination projector 2 is located. Surfaces 2 to 3 is the preferred beamsplitter for the eye alignment system. Surfaces 4 to 8 comprise Group 1; Surfaces 9 to 13 comprise Group 2; Surface 14 is the aperture stop; Surfaces 15 to 19 comprise Group 3; Surfaces 20 to 24 comprise Group 4; Surface 25 is the image plane. The spacing between the end of Group 4 (Surface 24) and the image plane is 59.99 mm, large enough to place an optional beamsplitter or rotary wheel of the detection system. The aperture stop diameter changes its size through zoom to maintain a fixed image f/#=15, and it's located at a fixed distance to Group 3, and moves along with Group 3 during the zoom motion.

Figure 15:
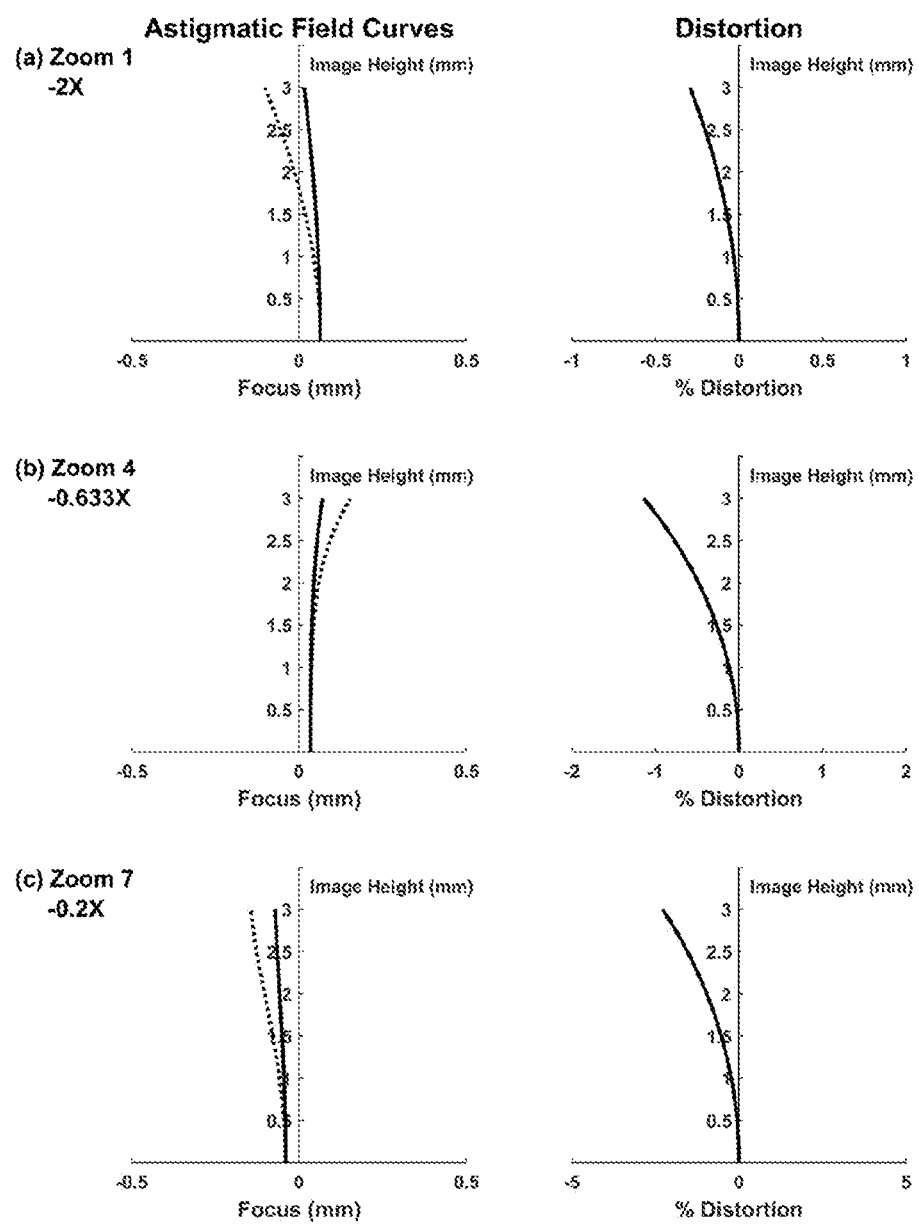
FIG. 15 a-c present astigmatic field curves and distortion of the Embodiment 2 at three representative zoom positions Zoom 1 (−2×), Zoom 4 (−0.633×) and Zoom 7 (−0.2×).

FIG. 15 a-c present the Embodiment 2 astigmatic field curves on the left and distortion on the right at three representative zoom positions: Zoom 1 (-2×), Zoom 4 (-0.633×) and Zoom 7 (-0.2×). In the field curves, the dashed line is for tangential field points, and the solid line is for sagittal field points.

Figure 16:
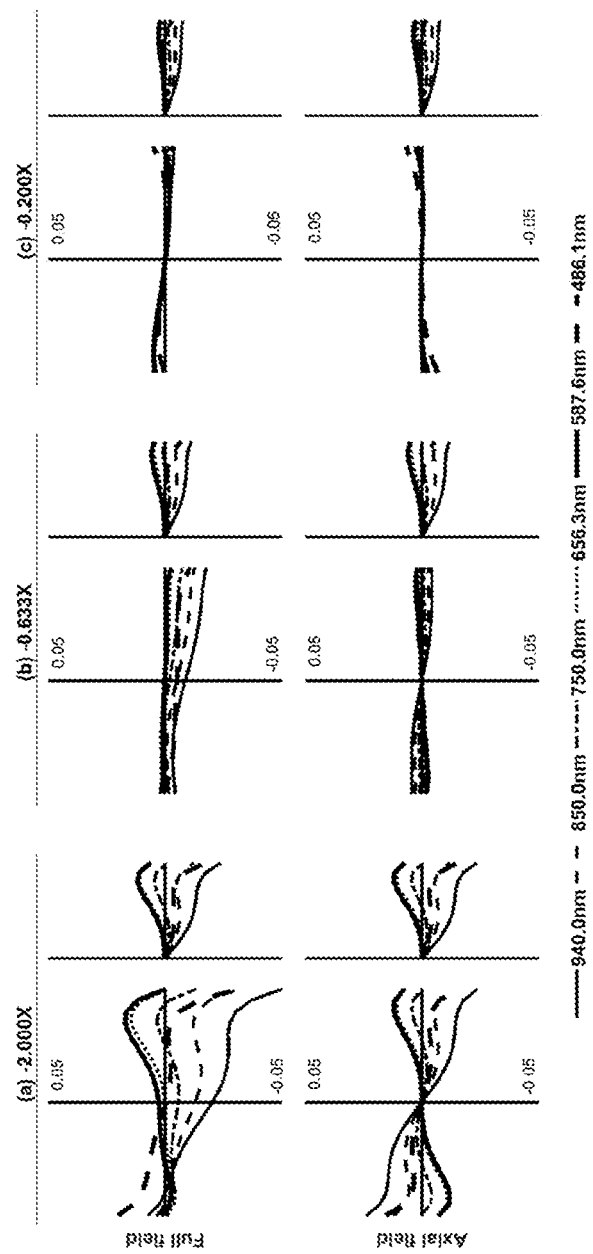
FIG. 16 a-c present the transverse ray plots of Embodiment 2 at three zoom positions. The overlap of some wavelengths with transverse ray errors close to zero at some subplots indicates good color aberration correction.

FIG. 16 a-c present the transverse ray plots of Embodiment 2 at the axial and full field points of three representative zoom positions: Zoom 1 (-2×), Zoom 4 (-0.633×) and Zoom 7 (-0.2×). For each zoom position, the tangential fields are on the left, and the sagittal fields are on the right. The overlap of some wavelengths with transverse ray errors close to zero at some subplots indicates good color aberration correction.

Figure 17:
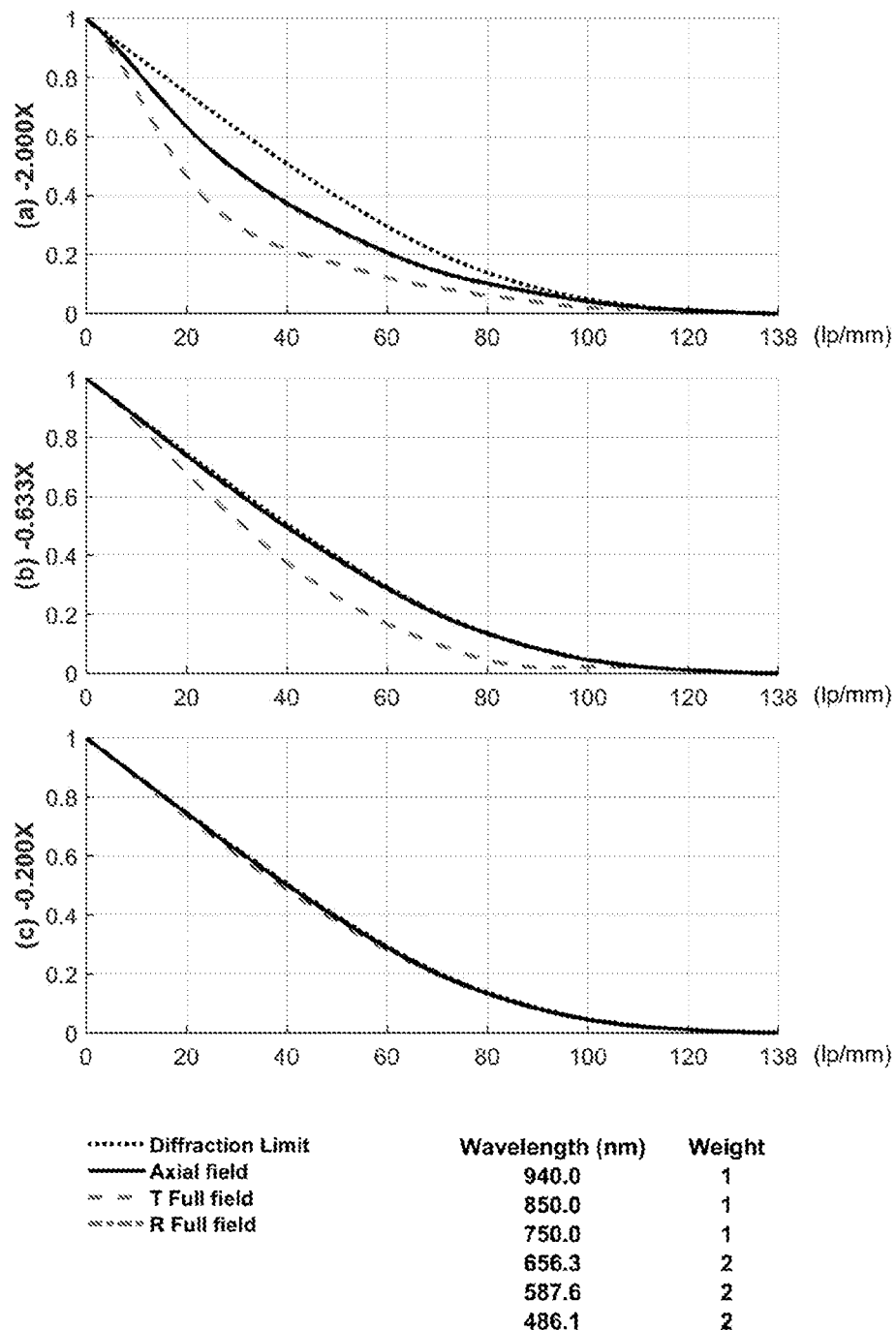
FIG. 17 presents the modulation transfer function (MTF) plots of Embodiment 2 at three zoom positions.

FIG. 17 presents the modulation transfer function (MTF) plots of Embodiment 2 of three representative zoom positions: Zoom 1 (-2×), Zoom 4 (-0.633×) and Zoom 7 (-0.2×).

Embodiment 3

Figure 18:
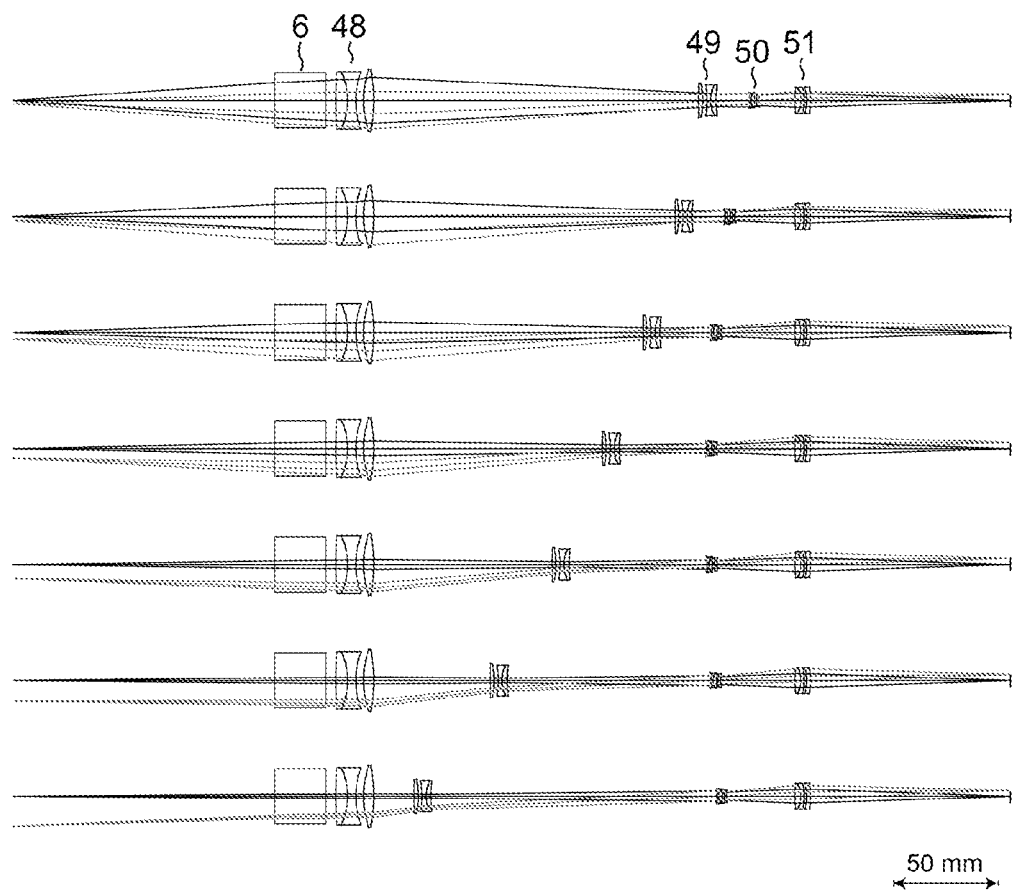
FIG. 18 presents the zoom motion trajectory of Embodiment 3 of a PNNP zoom lens system optimized for visible and near infrared spectra up to 850 nm.
Figure 19:
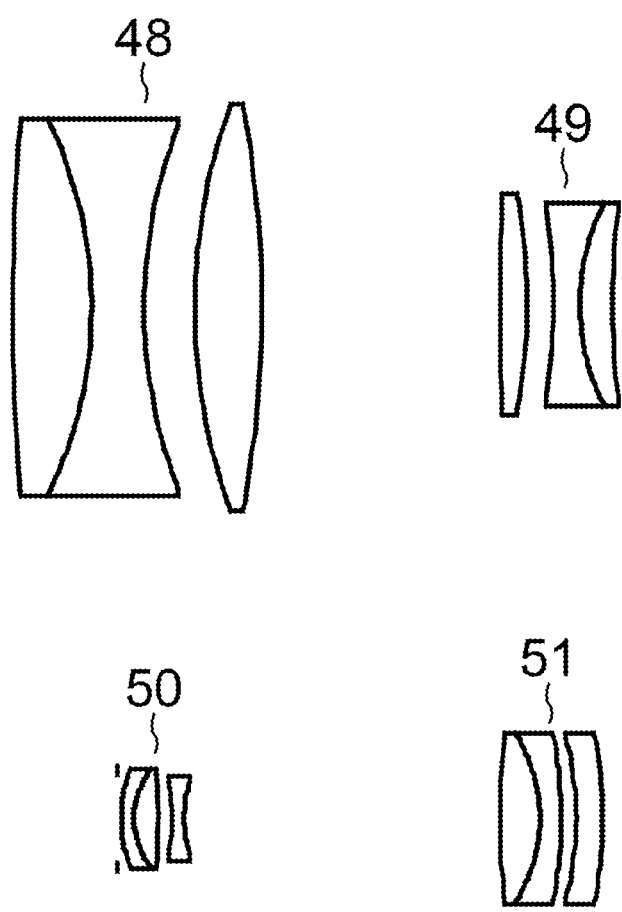
FIG. 19 represents the detailed design forms of each lens group in Embodiment 3.

FIG. 18 presents the zoom motion trajectory of Embodiment 3 of the zoom lens system optimized for visible and near infrared spectra up to 850 nm, for a sensor with the diagonal length of 6 mm. The zoom motion trajectory in FIG. 18 is shown for magnifications of −2×, −1.363×, −0.928×, −0.633×, −0.431×, −0.294× and −0.2×, from Zoom 1 to Zoom 7. This embodiment comprises four zoom groups. 48 is Group 1, and its position is fixed. 49 is Group 2, which is moveable during zoom. 50 is Group 3, which is moveable during zoom. 51 is Group 4 and its position is fixed. This specific embodiment of the four zoom groups has a PNNP configuration. FIG. 19 represents the detailed design forms of each lens group in FIG. 18.

The numerical details of Embodiment 3 are listed in Table 3, and the length values are in units of mm. The variable data during zoom are also listed.

TABLE 3

| Surface Number | Radius of curvature | Thickness | $n_d$ | $V_d$ | Semi-Aperture |
|---|---|---|---|---|---|
| Object | Infinity | 20 | | | |
| 1 | Infinity | 10 | | | 12.00 |
| 2 | Infinity | 25.4 | 1.516800 | 64.1673 | 12.15 |
| 3 | Infinity | 5 | | | 12.50 |
| 4 | 158.8559 | 5.9748 | 1.618000 | 63.3897 | 12.91 |
| 5 | −32 | 4 | 1.613360 | 44.4937 | 12.96 |
| 6 | 37.6163 | 3.8468 | | | 13.08 |
| 7 | 44.8912 | 5.0710 | 1.622992 | 58.1658 | 14.10 |
| 8 | −79.7223 | D8 | | | 14.14 |
| 9 | 343.2892 | 2 | 1.607381 | 56.6501 | 7.59 |
| 10 | −43.2399 | 2 | | | 7.48 |
| 11 | −42.9213 | 2 | 1.806100 | 40.8999 | 6.92 |
| 12 | 17 | 2.5 | 1.784720 | 25.7566 | 6.66 |
| 13 | 61.9019 | D13 | | | 6.57 |
| 14-Stop | Infinity | 0.3 | | | 3.32 |
| 15 | 9.7514 | 1 | 1.516400 | 64.0600 | 3.35 |
| 16 | 5.8812 | 1.8 | 1.572500 | 57.5493 | 3.22 |
| 17 | −51.6467 | 1 | | | 3.13 |
| 18 | −26.7999 | 1 | 1.713003 | 53.8316 | 2.92 |
| 19 | 9.4622 | D19 | | | 2.79 |
| 20 | 54.9762 | 3.0155 | 1.638539 | 55.3800 | 5.81 |
| 21 | −11.8020 | 1.6094 | 1.613360 | 44.4937 | 5.83 |
| 22 | −32.0587 | 1.1700 | | | 5.85 |
| 23 | −22.6087 | 1.9552 | 1.784720 | 25.6800 | 5.75 |
| 24 | −34.6373 | 99.1905 | | | 5.88 |
| 25-Image | Infinity | | | | 3.00 |

Variable data

| Zoom | Magnification | Object full diagonal length | Stop semi-aperture (SA14) | D8 | D13 | D19 |
|---|---|---|---|---|---|---|
| Z1 | −2X | 3.00 | 3.32 | 161.4346 | 16.1326 | 18.0000 |
| Z2 | −1.363X | 4.40 | 2.73 | 149.6261 | 16.0000 | 29.9410 |
| Z3 | −0.928X | 6.46 | 2.39 | 133.7051 | 25.1937 | 36.6683 |
| Z4 | −0.633X | 9.49 | 2.27 | 113.5236 | 42.8587 | 39.1849 |
| Z5 | −0.431X | 13.92 | 2.29 | 88.5379 | 68.1640 | 38.8653 |
| Z6 | −0.294X | 20.44 | 2.39 | 57.8085 | 100.8791 | 36.8796 |
| Z7 | −0.2X | 30.00 | 2.53 | 20.0000 | 141.5325 | 34.0346 |

The overall length of Embodiment 3 from the front surface of the beamsplitter (Surface 2) to the image plane is 365.4 mm From the object side to the image side, Surface 1 is a dummy surface, where the edge of the central opening aperture 23 of the illumination projector 2 is located. Surfaces 2 to 3 is the preferred beamsplitter for the eye alignment system. Surfaces 4 to 8 comprise Group 1; Surfaces 9 to 13 comprise Group 2; Surface 14 is the aperture stop; Surfaces 15 to 19 comprise Group 3; Surfaces 20 to 24 comprise Group 4; Surface 25 is the image plane. The spacing between the end of Group 4 (Surface 24) and the image plane is 99.19 mm, large enough to place an optional beamsplitter or rotary wheel of the detection system. The aperture stop diameter changes its size through zoom to maintain a fixed image f/#=15, and it's located at a fixed distance to Group 3, and moves along with Group 3 during the zoom motion.

Figure 20:
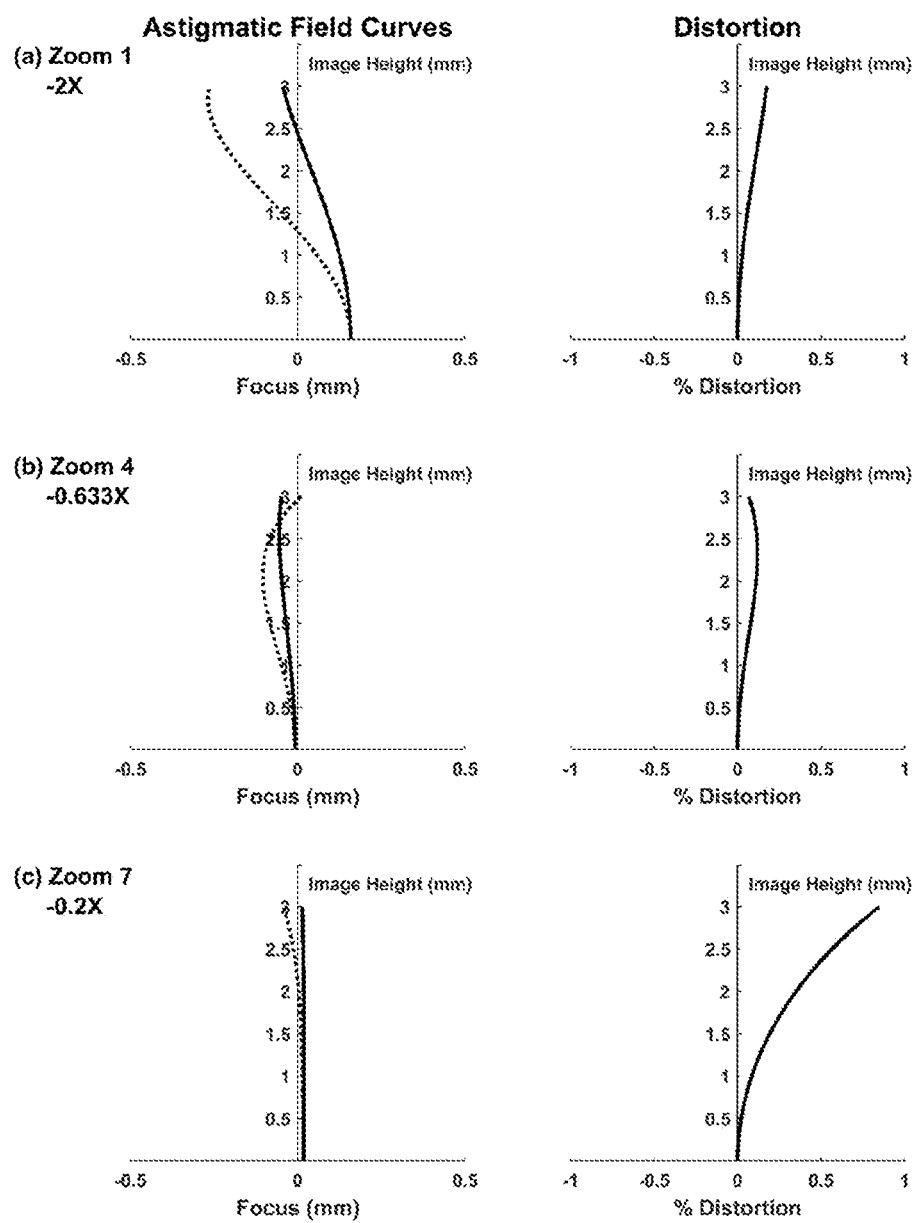
FIG. 20 a-c present astigmatic field curves and distortion of the Embodiment 3 at three representative zoom positions of Zoom 1 (−2×), Zoom 4 (−0.633×) and Zoom 7 (−0.2×).

FIG. 20 *a-c* present the Embodiment 3 astigmatic field curves on the left and distortion on the right at three representative zoom positions: Zoom 1 (−2×), Zoom 4 (−0.633×) and Zoom 7 (−0.2×). In the field curves, the dashed line is for tangential field points, and the solid line is for sagittal field points.

Figure 21:
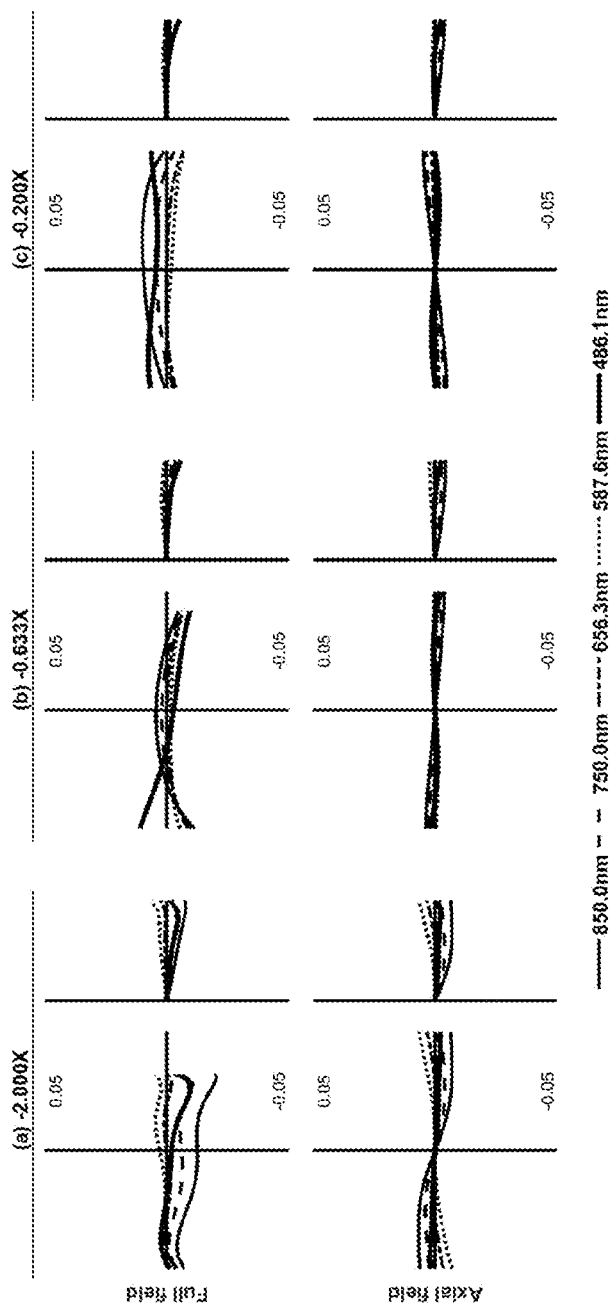
FIG. 21 a-c present the transverse ray plots of Embodiment 3 at three zoom positions. The overlap of some wavelengths with transverse ray errors close to zero at some subplots indicates good color aberration correction.

FIG. 21 *a-c* present the transverse ray plots of Embodiment 3 at the axial and full field points of three representative zoom positions: Zoom 1 (−2×), Zoom 4 (−0.633×) and Zoom 7 (−0.2×). For each zoom position, the tangential fields are on the left, and the sagittal fields are on the right. The overlap of some wavelengths with transverse ray errors close to zero at some subplots indicates good color aberration correction.

Figure 22:
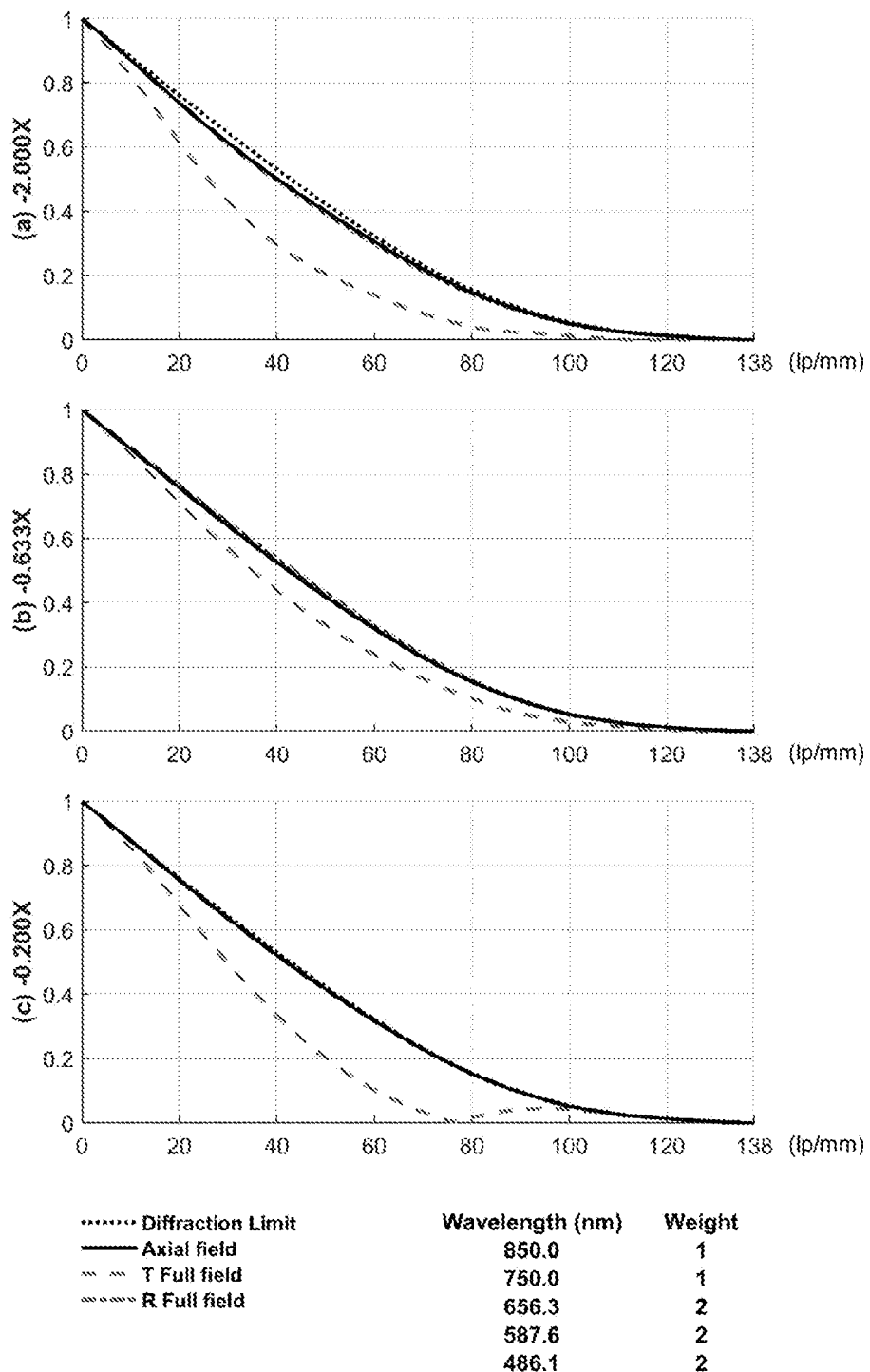
FIG. 22 presents the modulation transfer function (MTF) plots of Embodiment 3 at three zoom positions.

FIG. 22 presents the modulation transfer function (MTF) plots of Embodiment 3 of three representative zoom positions: Zoom 1 (−2×), Zoom 4 (−0.633×) and Zoom 7 (−0.2×).

Embodiment 4

Figure 23:
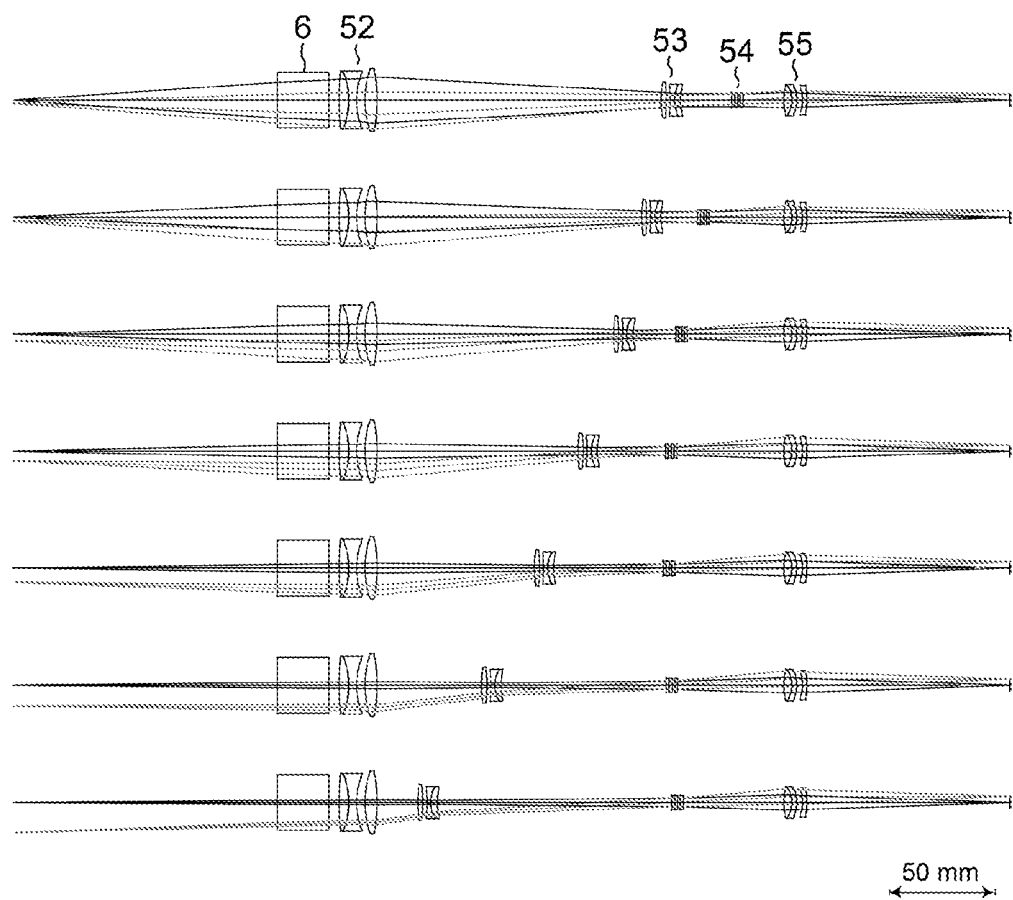
FIG. 23 presents the zoom motion trajectory of Embodiment 4 of a PNNP zoom lens system optimized for visible and near infrared spectra up to 940 nm.
Figure 24:
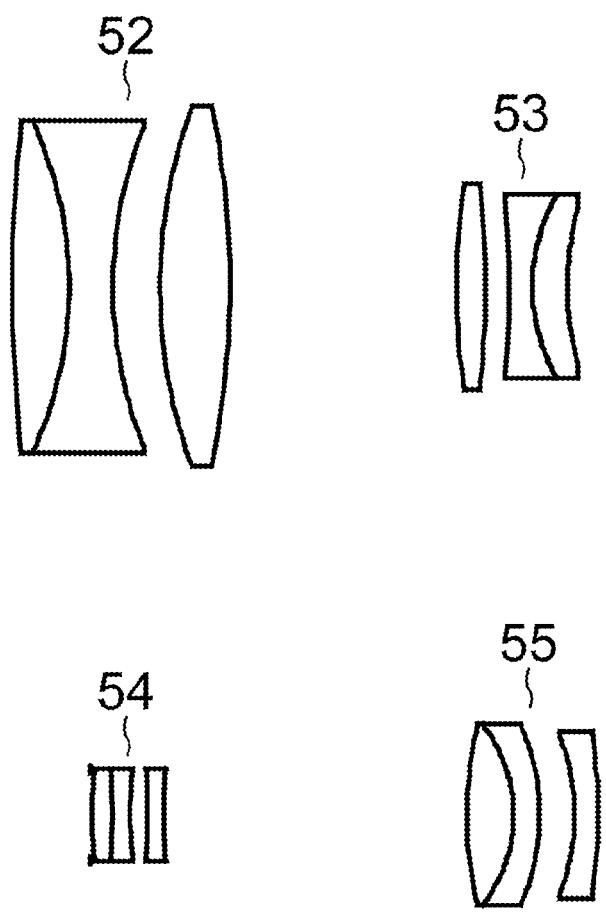
FIG. 24 represents the detailed design forms of each lens group in Embodiment 4.

FIG. 23 presents the zoom motion trajectory of Embodiment 4 of the zoom lens system optimized for visible and near infrared spectra up to 940 nm, for a sensor with the diagonal length of 6 mm. The zoom motion trajectory in FIG. 23 is shown for magnifications of −2×, −1.363×, −0.928×, −0.633×, −0.431×, −0.294× and −0.2×, from Zoom 1 to Zoom 7. This embodiment comprises four zoom groups. 52 is Group 1, and its position is fixed. 53 is Group 2, which is moveable during zoom. 54 is Group 3, which is moveable during zoom. 55 is Group 4 and its position is fixed. This specific embodiment of the four zoom groups has a PNNP configuration. FIG. 24 represents the detailed design forms of each lens group in FIG. 23.

The numerical details of Embodiment 4 are listed in Table 4, and the length values are in units of mm. The variable data during zoom are also listed.

TABLE 4

| Surface Number | Radius of curvature | Thickness | $n_d$ | $V_d$ | Semi-Aperture |
|---|---|---|---|---|---|
| Object | Infinity | 120 | | | |
| 1 | Infinity | 10 | | | 11.92 |
| 2 | Infinity | 25.4 | 1.516800 | 64.1673 | 12.07 |
| 3 | Infinity | 5 | | | 12.50 |
| 4 | 128.7867 | 4.8515 | 1.603110 | 60.5968 | 12.92 |
| 5 | −33.4170 | 3.7632 | 1.613360 | 44.4937 | 12.94 |
| 6 | 36.3573 | 4.0087 | | | 13.03 |
| 7 | 43.8239 | 6 | 1.618000 | 63.3897 | 14.12 |
| 8 | −74.7978 | D8 | | | 14.18 |
| 9 | 54.6852 | 2.5 | 1.607381 | 56.6501 | 7.94 |
| 10 | −75.7489 | 2 | | | 7.72 |
| 11 | −82.5822 | 2 | 1.772499 | 49.5984 | 7.08 |
| 12 | 15.5909 | 3 | 1.805182 | 25.4320 | 6.60 |
| 13 | 25.3578 | D13 | | | 6.29 |
| 14-Stop | Infinity | 0.1 | | | SA14 |
| 15 | 31.5491 | 1.5 | 1.654120 | 39.7001 | 3.18 |
| 16 | −100 | 1.5 | 1.607381 | 56.6501 | 3.16 |
| 17 | 35.2591 | 1.1901 | | | 3.12 |
| 18 | −94.9521 | 1.5 | 1.620053 | 36.4309 | 3.14 |
| 19 | 70.5480 | D19 | | | 3.18 |
| 20 | 32.7174 | 4 | 1.496999 | 81.5459 | 6.97 |
| 21 | −12.3351 | 2.2 | 1.568827 | 55.9758 | 6.95 |
| 22 | −19.3351 | 3 | | | 7.01 |
| 23 | −18.3490 | 2 | 1.691002 | 54.7084 | 6.36 |

TABLE 4-continued

| | | | | | |
|---|---|---|---|---|---|
| 24 | −47.1951 | 100 | | | 6.45 |
| 25-Image | Infinity | | | | 3.01 |

| | | | Variable data | | | |
|---|---|---|---|---|---|---|
| Zoom | Magnification | Object full diagonal length | Stop semi-aperture (SA14) | D8 | D13 | D19 |
| Z1 | −2X | 3.00 | 3.17 | 139.7612 | 25.1253 | 20.0000 |
| Z2 | −1.363X | 4.40 | 2.58 | 130.1361 | 18.0000 | 36.7504 |
| Z3 | −0.928X | 6.46 | 2.19 | 116.4054 | 20.9138 | 47.5673 |
| Z4 | −0.633X | 9.49 | 2.01 | 98.8448 | 33.3186 | 52.7232 |
| Z5 | −0.431X | 13.92 | 1.98 | 77.4206 | 53.7269 | 53.7390 |
| Z6 | −0.294X | 20.44 | 2.03 | 51.5055 | 81.1057 | 52.2753 |
| Z7 | −0.2X | 30.00 | 2.13 | 20.0000 | 115.3439 | 49.5427 |

The overall length of Embodiment 4 from the front surface of the beamsplitter (Surface 2) to the image plane is 360.4 mm From the object side to the image side, Surface 1 is a dummy surface, where the edge of the central opening aperture 23 of the illumination projector 2 is located. Surfaces 2 to 3 is the preferred beamsplitter for the eye alignment system. Surfaces 4 to 8 comprise Group 1; Surfaces 9 to 13 comprise Group 2; Surface 14 is the aperture stop; Surfaces 15 to 19 comprise Group 3; Surfaces 20 to 24 comprise Group 4; Surface 25 is the image plane. The spacing between the end of Group 4 (Surface 24) and the image plane is 100.00 mm, large enough to place an optional beamsplitter or rotary wheel of the detection system. The aperture stop diameter changes its size through zoom to maintain a fixed image f/#=15, and it's located at a fixed distance to Group 3, and moves along with Group 3 during the zoom motion.

Figure 25:
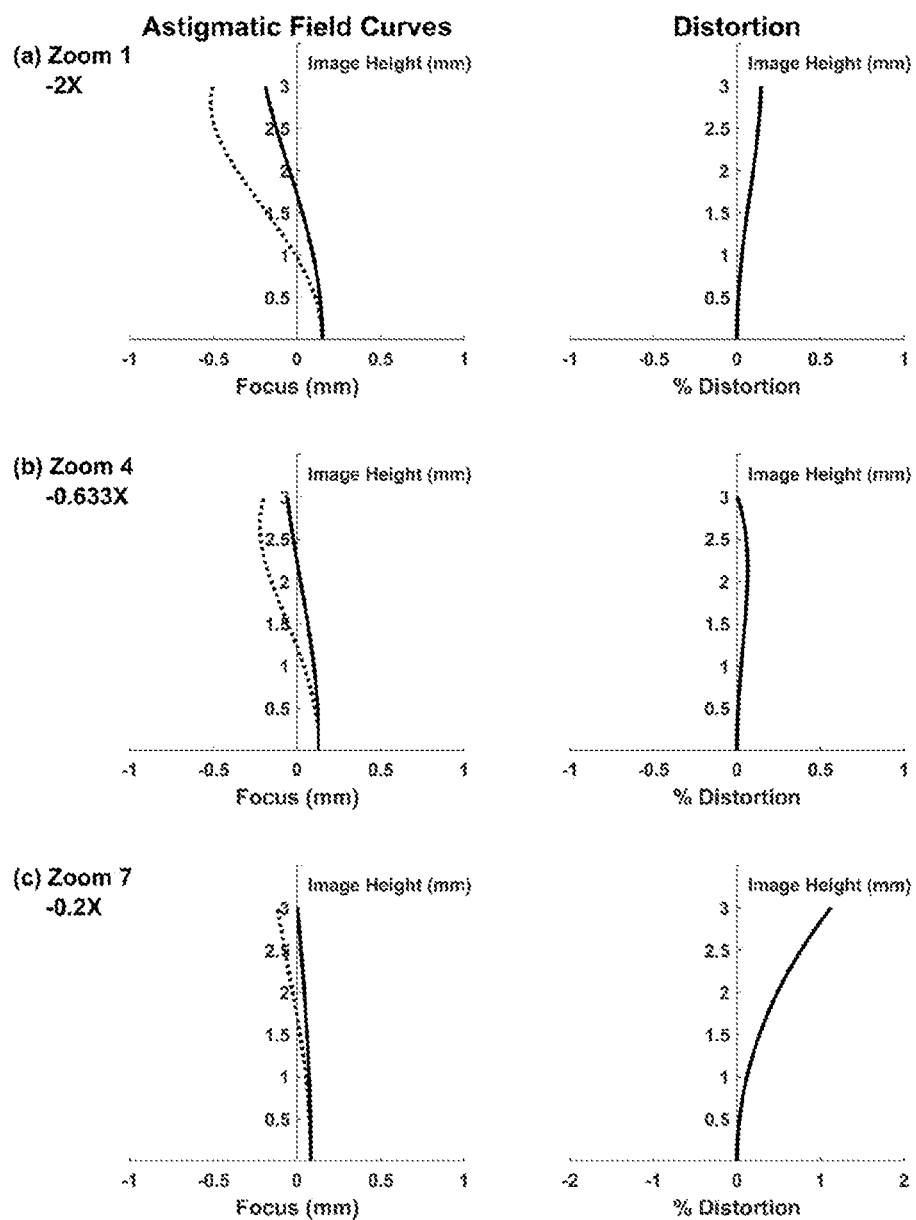
FIG. 25 a-c present astigmatic field curves and distortion of the Embodiment 4 at three representative zoom positions of Zoom 1 (−2×), Zoom 4 (−0.633×) and Zoom 7 (−0.2×).

FIG. 25 a-c present the Embodiment 4 astigmatic field curves on the left and distortion on the right at three representative zoom positions: Zoom 1 (−2×), Zoom 4 (−0.633×) and Zoom 7 (−0.2×). In the field curves, the dashed line is for tangential field points, and the solid line is for sagittal field points.

Figure 26:
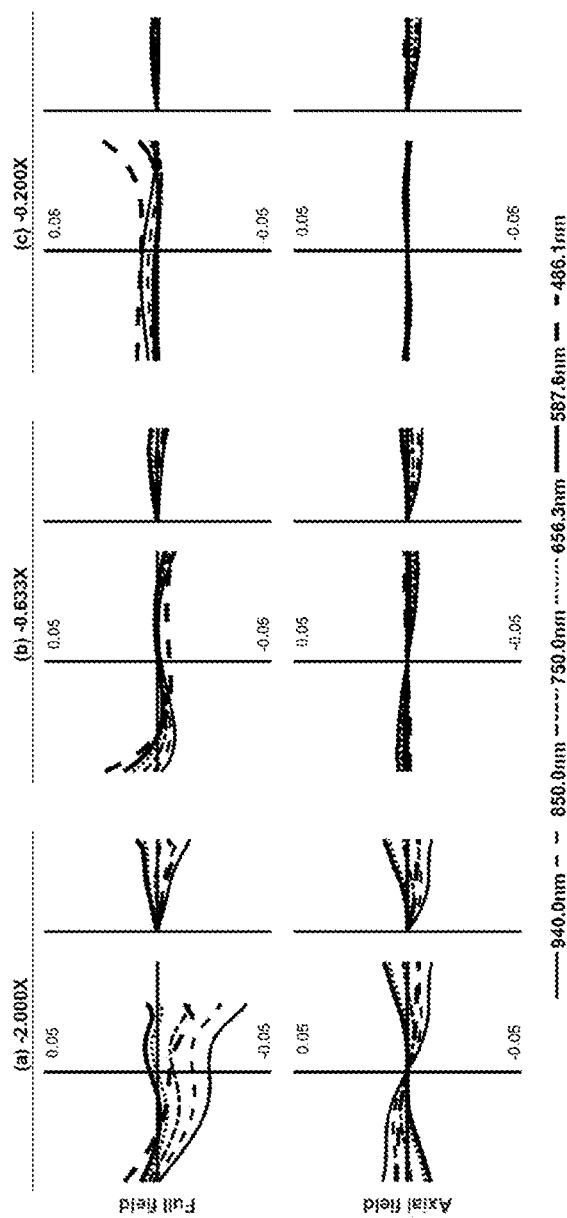
FIG. 26 a-c present the transverse ray plots of Embodiment 4 at three zoom positions. The overlap of some wavelengths with transverse ray errors close to zero at some subplots indicates good color aberration correction.

FIG. 26 a-c present the transverse ray plots of Embodiment 4 at the axial and full field points of three representative zoom positions: Zoom 1 (−2×), Zoom 4 (−0.633×) and Zoom 7 (−0.2×). For each zoom position, the tangential fields are on the left, and the sagittal fields are on the right. The overlap of some wavelengths with transverse ray errors close to zero at some subplots indicates good color aberration correction.

Figure 27:
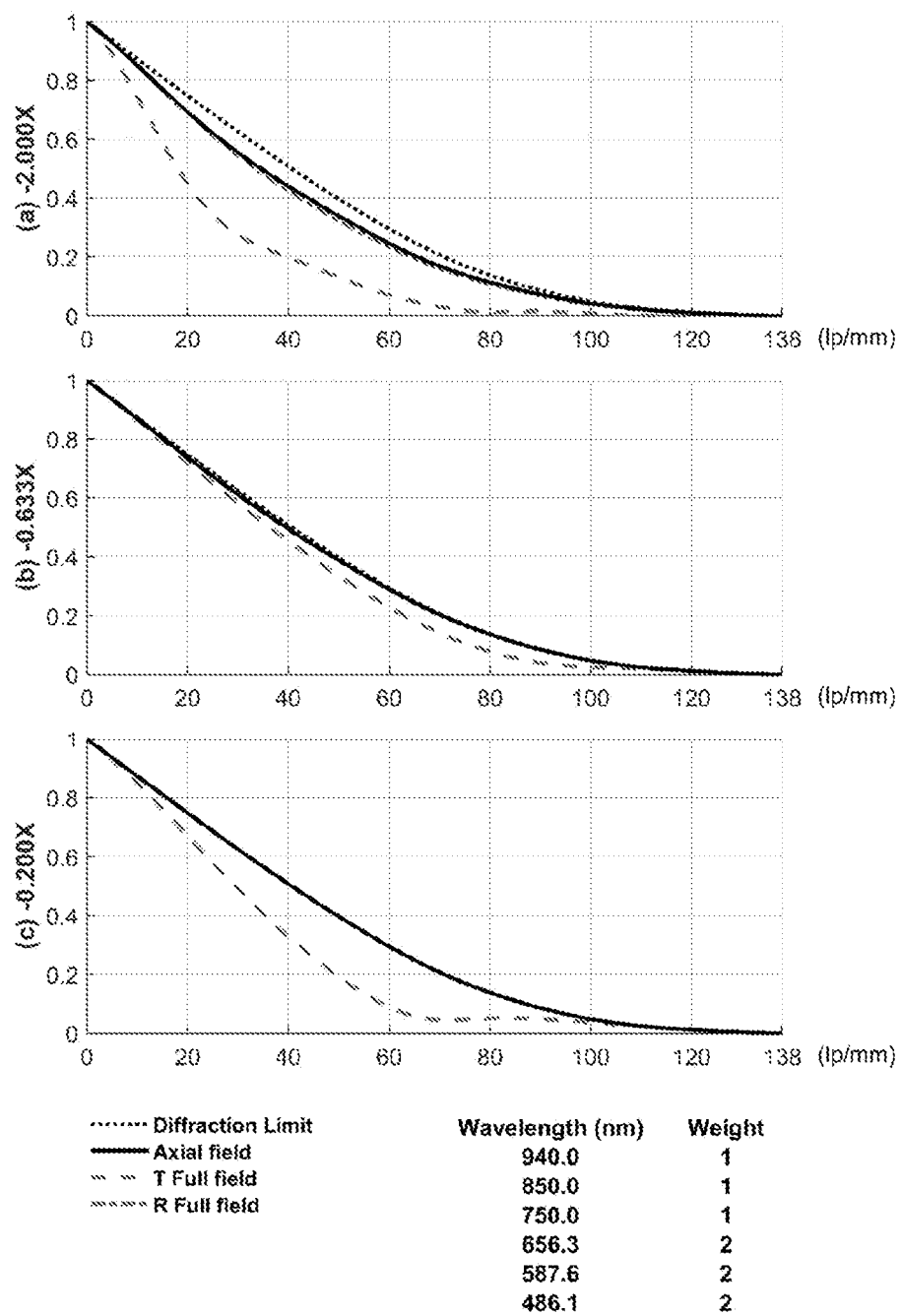
FIG. 27 presents the modulation transfer function (MTF) plots of Embodiment 4 at three zoom positions.

FIG. 27 presents the modulation transfer function (MTF) plots of Embodiment 4 of three representative zoom positions: Zoom 1 (−2×), Zoom 4 (−0.633×) and Zoom 7 (−0.2×).

In the preferred setup for the conical topography measurement, the subject is positioned properly and fixates on the alignment light source to align the eye with the instrument. Light from the illumination projector is directed toward the eye of the subject, and the reflected pattern is collected into the zoom lens system and reflected images are recorded. The setup geometry, the reflected image pattern and the corresponding magnification are used to calculate the geometrical shape of the cornea to generate a corneal topography map. Since a full view of the cornea is preferred to analyze corneal topography, the system is usually operated with a low magnification for this measurement.

Tear breakup time (TBUT) is evaluated in this invention by measuring the time interval immediately after a blink and the occurrence of a disrupted or distorted spot or area of the grid or ring pattern of the reflected images off the cornea with a low magnification to cover a substantial area of the cornea.

Tear meniscus height (TMH) in this invention is evaluated by zooming in with a high magnification and record an image of the lower eyelid margin with the tear meniscus. The TMH is calculated based on the magnification.

Bulbar redness can be evaluated either locally or globally with the instrument disclosed in this invention. The global bulbar redness is measured by taking an image of the ocular surface with a low magnification, such that both the nasal and temporal conjunctivae covering the sclera are within the field of view. Certain areas of the exposed bulbar conjunctiva are selected as the region of interest for bulbar redness analysis, and the number of blood vessels, blood vessel width distribution, the ratio of the area of blood vessel versus the total region of interest, or other degree-of-redness parameters are evaluated to quantify bulbar redness. If there are specific regions of clinical interest, the system can be zoomed in, and the bulbar redness can be evaluated locally with a higher magnification to reveal the fine features of the blood vessels. Similarly, hyperemia of palpebral conjunctiva can also be quantitatively evaluated.

Meibography images are obtained by taking reflective images with illumination after everting the upper or lower eyelids to reveal the inner surface of the eyelids. A low magnification is used for overall evaluation of the meibomian glands distribution. However, if there are specific regions of clinical interest, for example, for individual meibomian glands atrophy evaluation, the system can be zoomed in to obtain higher magnification images.

In the prior art, direct illumination meibography are done with near infrared spectrum. In this invention, meibography is done with visible and near infrared spectra. In a preferred embodiment, the broad band illumination is used for meibography, and both the visible and the near infrared images can be used to reveal the meibomian glands structures and distribution. Further, two indices to enhance the contrast of the meibomian glands with neighboring tissues are introduced in this invention. The first index is the "Difference Meibomian Gland Index" (DMGI), $$DMGI = \rho_r - \rho_n \tag{1}$$

where $\rho_r$ and $\rho_n$ are the irradiance reflectance values of red and near infrared color channels calculated at each pixel. The irradiance reflectance includes light of both specular reflection and scattering that is collected by the apparatus.

The second index is the "Normalized Difference Meibomian Gland Index" (NDMGI), $$NDMGI = (\rho_r - \rho_n)/(\rho_r + \rho_n) \tag{2}$$

These indices are evaluated at each pixel, so an entire frame of a meibomian gland image can be analyzed to enhance the contrast of the meibomian glands with respect to neighboring tissues. Other indices contain visible and near infrared spectra information, such as a simple ratio of $\rho_r/\rho_n$ could also be used to increase the contrast.

High magnification imaging is used in this invention for meibomian gland orifices and eyelashes examination. Individual meibomian glands can be inspected when the system is zoomed in, which would enable examination of potential clogging by solidified lipids, or potential crusting at the base of the eyelashes due to blepharitis, etc.

In the prior art, the lipid layer thickness is evaluated by inspecting the reflected colors off the cornea, due to the interference of multiple reflection at the air-lipid layer-aqueous layer interface. In this invention, the lipid layer thickness is not determined by the color match in the visible spectrum, which usually is evaluated in red, green and blue three color channels, as was done in the prior art, but rather by the multispectral reflectance match, including both the visible and NIR spectra. One preferred embodiment of the multispectral reflectance analysis involves red, green, blue (RGB) and NIR four detection channels. The added NIR color channel will increase the accuracy of the lipid layer thickness determination, which is especially useful for thick lipid measurement. The multispectral irradiance reflectance for a range of pre-selected thickness values of the lipid layer thickness, for example, 0 to 500 nm, with an increment of 0.2 nm could be analyzed, and the resultant multispectral reflectance of RGB and NIR four channels could be stored as a lookup table in the analysis software. Each pixel in the image taken from the apparatus in the invention will have RGB and NIR four values, one in each detection channel. This invention introduces the sum of the q-th order multispectral mismatch:

$$SUM=|R_m-R_{lt}|^q+|G_m-G_{lt}|^q+|B_m-B_{lt}|^q+|NIR_m-NIR_{lt}|^q \quad (3),$$

where the subscript "m" stands for measured data, and the subscript "lt" stands for the lookup table. The superscript "q" is a positive integer, such as 1, 2, 3, etc. Usually, q=1, or q=2 is chosen to quantify the multispectral mismatch. SUM can be evaluated at each pixel, and the lipid layer thickness value that minimizes SUM can be used to estimate the physical thickness of the lipid layer. Other similar statistical parameters, such as the square root of SUM that evaluates visible and near infrared multispectral reflectance matching errors, could also be employed for the lipid layer thickness determination.

A micro thermal camera 22 in FIG. 3, is employed to characterize the thermal dynamics of the ocular surface. Preferably, the thermal camera operates in the long wave infrared (LWIR) range of about 7.5 µm to 14 µm. The thermal camera is placed at a small aperture close to the central aperture for the main optical system with a zoom lens group. Preferably, the thermal camera aperture on the illuminator has a diameter of smaller than 15 mm. For example, one embodiment of the micro thermal camera is based on the FLIR Lepton LWIR micro thermal camera (FLIR Systems, Wilsonville, Oreg.). Even though the LWIR thermal camera and the visible-NIR optical system are not coaxial, they are arranged to be paraxial in this invention so that simultaneous measurement of the tear film evolution and thermal dynamical profile of the ocular surface is possible. Further, with properly chosen magnification and field of view of the micro thermal camera, the thermal effect of tear breakup could be directly investigated with this instrument. This will enable an operator to directly study the relation of tear break up and the ocular surface thermal dynamics and characterize the thermal profile of a subject.

Blink rate in this invention is monitored by an optional separate video camera 19, as shown in FIG. 2, which is connected to the rest of system by an electric wire or wireless communication means, such as Bluetooth, or Wi-Fi. The video camera can be placed at the convenience of the operator, facing the subject under test. Preferably the field of view of the camera is large enough to cover a relatively large range of variation of the subject positions, subject heights, chair heights, chair positions, etc to allow flexible subject positions. The frame rate is no less than 5 frames per second, so the camera is fast enough to detect the downstroke and upstroke of the eyelids movements during a blink. Also preferably, the monitoring process is done when the operator is chatting with the subject, and the subject is not using any other measurement instrument, such as instrument 1, in order to obtain more natural blinks. The recorded blink video of the movement of the eyelids is subsequently analyzed by the computer.

The invention has been described in detail with particular reference to certain preferred embodiments thereof, but it will be understood that variations and modifications can be effected within the spirit and scope of the invention.

What is claimed is:

1. A multifunctional ophthalmic instrument for assessing health of an ocular surface and adjacent structures, said instrument comprising:
    an illumination projector with an anterior opening toward an eye and an aperture in a posterior end of said projector, wherein said illumination projector contains broadband light sources, covering visible and near infrared spectra, to illuminate an ocular surface and adjacent structures of said eye and project a pattern on said ocular surface;
    a zoom lens system with continuously variable magnification to form images of said ocular surface and adjacent structures, located posterior to said aperture of said illumination projector, wherein said zoom lens system has color aberration correction covering visible and near infrared spectra, wherein said zoom lens system has at least two moving groups comprising a variator and a compensator, wherein said zoom lens system comprises in sequence, a front positive lens group, a middle negative lens group, a middle positive lens group and a back negative lens group, wherein the middle negative lens group and the middle positive lens group are moving during zoom, and the front positive lens group and the back negative lens group are fixed during zoom, wherein an aperture stop is set to move along with the middle positive lens group,
    a detection system to record said images;
    wherein said detection system is sensitive in visible and near infrared spectra and configured to measure Difference Meibomian Gland Index (DMGI)=$\rho_r-\rho_n$, wherein $\rho_r$ and $\rho_n$ are irradiance reflectance values of red and near infrared color channels at each pixel, and
    wherein said zoom lens system zooms in to inspect with object resolution of at least 0.02 mm and zooms out to evaluate at least a majority of said ocular surface and adjacent structures of said eye;
    and
    a computer to display and analyze said images.

2. The apparatus of claim 1, wherein said illumination projector has a form of a conical frustum, wherein said illumination projector comprises:
    an illumination source panel comprising visible and near infraredlight-emitting diodes (LEDs);
    an optical diffusing panel with one or more layers of translucent materials;
    a panel with a pattern to project on said ocular surface.

3. The apparatus of claim 1, wherein said illumination projector is a curved display comprising organic light-emitting diodes (OLEDs) to generate dynamically changing projection patterns.

4. The apparatus of claim 1, wherein an eye alignment system is used to provide a fixation target for an eye under assessment, wherein said eye alignment system comprises a light source and a beamsplitter, wherein said beamsplitter is placed between said aperture of said illumination projector and said zoom lens system, wherein said eye alignment system and said zoom lens system are aligned coaxially.

5. The apparatus of claim 4, wherein the light source of said eye alignment system is a single light-emitting diode (LED), or a light-emitting diode with a collimating lens group, or a low power laser in the visible spectrum, or an optical fiber with a collimating lens group.

6. The apparatus of claim 1, wherein a thermal camera is placed paraxially with said zoom lens system to measure a dynamical thermal change of said ocular surface, wherein said thermal camera operates in the long wave infrared wavelength range of 7.5 µm to 14 µm.

7. The apparatus of claim 1, wherein a separate video camera is used to monitor a blink rate of said eye, wherein said separate video camera is connected to said apparatus with a wire or wireless connection means.

8. The apparatus of claim 1, wherein said detection system comprises a detector, which is sensitive to visible and near infrared spectra.

9. The apparatus of claim 1, wherein said detection system comprises two detectors and a dichroic beamsplitter, wherein said dichroic beamsplitter splits light into one visible branch and one near infrared branch, wherein one of said detectors is sensitive to said one visible branch, and the other of said detectors is sensitive to said one near infrared branch.

10. A method of assessing ocular surface health using a multifunctional ophthalmic instrument according to claim 1, comprising:
    illuminating an ocular surface and adjacent structures of an eye with an illumination projector, covering visible and near infrared spectra; forming images of said ocular surface and adjacent structures of said eye with said zoom lens system;
    choosing a magnification by using said zoom lens system;
    recording images formed on said detector system;
    displaying and analyzing said images to determine ocular surface health with said computer.

11. The method of claim 10, further comprising aligning said ocular surface of said eye by requesting a subject to fixate on a light source of an eye alignment system comprising said light source and a beamsplitter, wherein said beamsplitter is placed between the aperture of said illumination projector and said zoom lens system and wherein said eye alignment system and said zoom lens system are aligned coaxially.

12. The method of claim 10, wherein analyzing comprises analyzing reflected images of said illumination projector off said ocular surface to determine a topography of said ocular surface.

13. The method of claim 10, wherein analyzing comprises evaluating a time interval between a last blink and an occurrence of a disrupted area of a pattern of reflected images of said illumination projector off said ocular surface to determine a tear breakup time.

14. The method of claim 10, wherein said magnification is a high magnification to inspect microscopic features, wherein said microscopic features include tear meniscus height, meibomian gland orifices, and bases of eyelashes.

15. The method of claim 10, wherein said analyzing comprises quantitatively evaluating a bulbar redness and a palpebral redness of the eye based on a conjunctival vascular distribution of said images.

16. The method of claim 10, wherein said analyzing comprises evaluating images of meibomian glands in the visible and near infrared spectra.

17. The method of claim 10, wherein said analyzing comprises determining lipid layer thickness by multispectral reflectance values of visible and near infrared channels of said detection system.

18. The method of claim 10, further comprising locating a thermal camera paraxially to said zoom lens system and analyzing said ocular surface by evaluating a dynamic thermal change of said ocular surface by said thermal camera.

19. The method of claim 10, further comprising locating a separate video camera facing said eye to monitor a blink rate of said eye based on a video of movements of an eyelid of said eye.

20. The device of claim 1, wherein said detection system is sensitive in visible and near infrared spectra and configured to measure Normalized Difference Meibomian Gland Index (NDMGI)=$(\rho_r-\rho_n)/(\rho_r+\rho_n)$, wherein $\rho_r$ and $\rho_n$ are irradiance reflectance values of red and near infrared color channels at each pixel.

21. A multifunctional ophthalmic instrument for assessing health of an ocular surface and adjacent structures, said instrument comprising:
    an illumination projector with an anterior opening toward an eye and an aperture in a posterior end of said projector, wherein said illumination projector contains broadband light sources, covering visible and near infrared spectra, to illuminate an ocular surface and adjacent structures of said eye and project a pattern on said ocular surface;
    a zoom lens system with continuously variable magnification to form images of said ocular surface and adjacent structures, located posterior to said aperture of said illumination projector, wherein said zoom lens system has color aberration correction covering visible and near infrared spectra, wherein said zoom lens system has at least two moving groups comprising a variator and a compensator, wherein said zoom lens system comprises in sequence, a front positive lens group, a first middle negative lens group, a second middle negative lens group and a back positive lens group, wherein the first middle negative lens group and the second middle negative lens group are moving during zoom, and the front positive lens group and the back positive lens group are fixed during zoom, wherein an aperture stop is set to move along with the second middle negative lens group,
    a detection system to record said images;
    wherein said detection system is sensitive in visible and near infrared spectra and configured to measure Difference Meibomian Gland Index (DMGI)=$\rho_r-\rho_n$, wherein $\rho_r$ and $\rho_n$ are irradiance reflectance values of red and near infrared color channels at each pixel, and
    wherein said zoom lens system zooms in to inspect with object resolution of at least 0.02 mm and zooms out to evaluate at least a majority of said ocular surface and adjacent structures of said eye;
    and
    a computer to display and analyze said images.

* * * * *